(12) United States Patent
Hafezi et al.

(10) Patent No.: US 11,149,123 B2
(45) Date of Patent: Oct. 19, 2021

(54) HIGHLY-SWELLABLE POLYMERIC FILMS AND COMPOSITIONS COMPRISING THE SAME

(71) Applicant: Otsuka America Pharmaceutical, Inc., Rockville, MD (US)

(72) Inventors: Hooman Hafezi, Redwood City, CA (US); Raymond Schmidt, San Francisco, CA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 306 days.

(21) Appl. No.: 14/763,217

(22) PCT Filed: Jan. 28, 2014

(86) PCT No.: PCT/US2014/013382
§ 371 (c)(1),
(2) Date: Jul. 24, 2015

(87) PCT Pub. No.: WO2014/120669
PCT Pub. Date: Aug. 7, 2014

(65) Prior Publication Data
US 2015/0361234 A1     Dec. 17, 2015

Related U.S. Application Data

(60) Provisional application No. 61/758,030, filed on Jan. 29, 2013.

(51) Int. Cl.
*C08J 5/18*     (2006.01)
*C08L 5/00*    (2006.01)
(Continued)

(52) U.S. Cl.
CPC ............... *C08J 5/18* (2013.01); *A61B 5/0538* (2013.01); *A61B 5/073* (2013.01); *A61B 5/4839* (2013.01);
(Continued)

(58) Field of Classification Search
CPC ........ C08J 5/18; C08J 9/0061; C08J 2333/02; C08J 2433/02; C08J 2305/04;
(Continued)

(56) References Cited

U.S. PATENT DOCUMENTS 1,548,459 A    8/1925   Hammer
2,587,158 A    2/1952   Hofberg
(Continued)

FOREIGN PATENT DOCUMENTS

CN    1588649    3/2005
CN    1650844    8/2005
(Continued)

OTHER PUBLICATIONS

Wang, X. et al "Resistance to Tracking and Erosion of Silicone Rubber Material under Various Types of Precipitation", Jpn. J. Appl. Phys. vol. 38 (1999) pp. 5170-5175.
(Continued)

*Primary Examiner* — Jacqueline Cheng
*Assistant Examiner* — Tho Q Tran
(74) *Attorney, Agent, or Firm* — Mannava & Kang, P.C.

(57) ABSTRACT

Highly-swellable polymeric films are provided. Aspects also include ingestible compositions that include the highly-swellable polymeric film and an ingestible component. Aspects further include methods of making and using the compositions.

29 Claims, 16 Drawing Sheets

(51) Int. Cl.

| | |
|---|---|
| *C08L 101/14* | (2006.01) |
| *C08L 33/02* | (2006.01) |
| *A61K 9/70* | (2006.01) |
| *C08L 5/04* | (2006.01) |
| *A61B 5/0538* | (2021.01) |
| *A61B 5/07* | (2006.01) |
| *A61B 5/00* | (2006.01) |
| *C08J 9/00* | (2006.01) |

(52) U.S. Cl.
CPC .......... *A61B 5/6861* (2013.01); *A61B 5/7282* (2013.01); *A61K 9/7007* (2013.01); *C08J 9/0061* (2013.01); *C08L 5/00* (2013.01); *C08L 5/04* (2013.01); *C08L 33/02* (2013.01); *C08L 101/14* (2013.01); *A61B 2562/12* (2013.01); *C08J 2305/04* (2013.01); *C08J 2333/02* (2013.01); *C08J 2433/02* (2013.01)

(58) Field of Classification Search
CPC ..... A61B 5/0538; A61B 5/073; A61B 5/4839; A61B 5/6861; A61B 5/7282; A61B 2562/12; C08L 5/04; C08L 33/02; C08L 101/14; C08L 5/00; A61K 9/7007
See application file for complete search history.

(56) References Cited

U.S. PATENT DOCUMENTS

| | | |
|---|---|---|
| 2,973,555 A | 3/1961 | Schwepke |
| 3,048,526 A | 8/1962 | Boswell |
| 3,079,824 A | 3/1963 | Schott |
| 3,096,248 A | 7/1963 | Rudzki |
| 3,176,399 A | 4/1965 | Marino et al. |
| 3,589,943 A | 6/1971 | Grubb et al. |
| 3,607,788 A | 9/1971 | Adolph |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,799,802 A | 3/1974 | Schneble, Jr. et al. |
| 3,828,766 A | 8/1974 | Krasnow |
| 3,837,339 A | 9/1974 | Aisenberg et al. |
| 3,849,041 A | 11/1974 | Knapp |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,139,589 A | 2/1979 | Beringer et al. |
| 4,143,770 A | 3/1979 | Grimmell et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,559,950 A | 12/1985 | Vaughan |
| 4,564,363 A | 1/1986 | Bagnall et al. |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,775,536 A | 10/1988 | Patell |
| 4,784,162 A | 11/1988 | Ricks |
| 4,793,825 A | 12/1988 | Benjamin et al. |
| 4,814,181 A | 3/1989 | Jordan et al. |
| 4,844,076 A | 7/1989 | Lesho |
| 4,847,090 A | 7/1989 | Della Posta et al. |
| 4,876,093 A | 10/1989 | Theeuwes et al. |
| 4,891,223 A | 1/1990 | Ambegaonakar et al. |
| 4,896,261 A | 1/1990 | Nolan |
| 4,900,552 A | 2/1990 | Sanvordeker et al. |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,018,335 A | 5/1991 | Yamamoto et al. |
| 5,079,006 A | 1/1992 | Urguhart |
| 5,110,441 A | 5/1992 | Kinlen et al. |
| 5,160,885 A | 11/1992 | Hannam et al. |
| 5,167,626 A | 12/1992 | Casper |
| 5,176,626 A | 1/1993 | Soehendra |
| 5,187,723 A | 2/1993 | Mueller |
| 5,213,738 A | 5/1993 | Hampton et al. |
| 5,218,343 A | 6/1993 | Stobbe et al. |
| 5,261,402 A | 11/1993 | DiSabito |
| 5,263,481 A | 11/1993 | Axelgaard et al. |
| 5,273,066 A * | 12/1993 | Graham .............. A01G 25/167 137/78.3 |
| 5,279,607 A | 1/1994 | Schentag et al. |
| 5,281,287 A | 1/1994 | Lloyd |
| 5,283,136 A | 2/1994 | Peled et al. |
| 5,288,564 A | 2/1994 | Klein |
| 5,305,745 A | 4/1994 | Zacouto |
| 5,310,301 A | 5/1994 | Aono |
| 5,318,557 A | 6/1994 | Gross |
| 5,331,953 A | 7/1994 | Andersson et al. |
| 5,394,882 A | 3/1995 | Mawhinney |
| 5,395,366 A | 3/1995 | D'Andrea et al. |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,458,994 A | 10/1995 | Nesselbeck et al. |
| 5,485,841 A | 1/1996 | Watkin et al. |
| 5,506,248 A | 4/1996 | Nikfar et al. |
| 5,551,020 A | 8/1996 | Flax et al. |
| 5,567,210 A | 10/1996 | Bates et al. |
| 5,596,302 A | 1/1997 | Mastrocola et al. |
| 5,600,548 A | 2/1997 | Nguyen et al. |
| 5,603,363 A | 2/1997 | Nelson |
| 5,634,468 A | 6/1997 | Platt |
| 5,645,063 A | 7/1997 | Straka et al. |
| 5,659,247 A | 8/1997 | Clements |
| 5,703,463 A | 12/1997 | Smith |
| 5,705,189 A | 1/1998 | Lehmann et al. |
| 5,724,432 A | 3/1998 | Bouvet et al. |
| 5,738,708 A | 4/1998 | Peachey et al. |
| 5,740,811 A | 4/1998 | Hedberg |
| 5,757,326 A | 5/1998 | Koyama et al. |
| 5,772,575 A | 6/1998 | Lesinski et al. |
| 5,792,048 A | 8/1998 | Schaefer |
| 5,802,467 A | 9/1998 | Salazar |
| 5,833,716 A | 11/1998 | Bar-Or |
| 5,842,324 A | 12/1998 | Grosskopf et al. |
| 5,845,265 A | 12/1998 | Woolston |
| 5,862,803 A | 1/1999 | Besson |
| 5,868,136 A | 2/1999 | Fox |
| 5,914,132 A | 6/1999 | Kelm et al. |
| 5,914,701 A | 6/1999 | Gersheneld et al. |
| 5,925,030 A | 7/1999 | Gross et al. |
| 5,957,854 A | 9/1999 | Besson et al. |
| 5,963,132 A | 10/1999 | Yoakum et al. |
| 5,974,124 A | 10/1999 | Schlueter, Jr. et al. |
| 5,981,166 A | 11/1999 | Mandecki |
| 5,999,846 A | 12/1999 | Pardey et al. |

(56) References Cited

U.S. PATENT DOCUMENTS

| | | |
|---|---|---|
| 6,018,229 A | 1/2000 | Mitchell et al. |
| 6,038,464 A | 3/2000 | Axelgaard et al. |
| 6,042,710 A | 3/2000 | Dubrow |
| 6,047,203 A | 4/2000 | Sackner |
| 6,068,465 A | 5/2000 | Wilson |
| 6,068,589 A | 5/2000 | Neukermans |
| 6,076,016 A | 6/2000 | Feierbach et al. |
| 6,081,734 A | 6/2000 | Batz |
| 6,091,975 A | 7/2000 | Daddona et al. |
| 6,095,985 A | 8/2000 | Raymond et al. |
| 6,115,636 A | 9/2000 | Ryan |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,317,714 B1 | 11/2001 | Del Castillo |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Nohl et al. |
| 6,394,997 B1 | 5/2002 | Lemelson |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,496,705 B1 | 12/2002 | Ng et al. |
| 6,526,315 B1 | 2/2003 | Inagawa |
| 6,531,026 B1 | 3/2003 | Takeichi et al. |
| 6,544,174 B2 | 4/2003 | West |
| 6,547,994 B1 | 4/2003 | Monkhouse et al. |
| 6,564,079 B1 | 5/2003 | Cory |
| 6,567,685 B2 | 5/2003 | Takamori et al. |
| 6,572,636 B1 | 6/2003 | Hagen et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,602,518 B2 | 8/2003 | Seielstad et al. |
| 6,605,038 B1 | 8/2003 | Teller |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,739,455 B2 | 5/2004 | Yamamoto et al. |
| 6,740,033 B1 | 5/2004 | Olejniczak et al. |
| 6,741,731 B1 | 5/2004 | Yamamoto et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,767,200 B2 | 7/2004 | Sowden et al. |
| 6,773,429 B2 | 8/2004 | Sheppard et al. |
| 6,800,060 B2 | 10/2004 | Marshall |
| 6,801,137 B2 | 10/2004 | Eggers et al. |
| 6,816,794 B2 | 11/2004 | Alvi |
| 6,822,554 B2 | 11/2004 | Vrijens et al. |
| 6,824,512 B2 | 11/2004 | Warkentin et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,888,337 B2 | 5/2005 | Sawyers |
| 6,889,165 B2 | 5/2005 | Lind et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,942,770 B2 | 9/2005 | Cai et al. |
| 6,946,156 B2 | 9/2005 | Bunick |
| 6,951,536 B2 | 10/2005 | Yokoi |
| 6,957,107 B2 | 10/2005 | Rogers et al. |
| 6,958,603 B2 | 10/2005 | Kondo |
| 6,960,617 B2 | 11/2005 | Omidian et al. |
| 6,968,153 B1 | 11/2005 | Heinonen |
| 6,977,511 B2 | 12/2005 | Patel et al. |
| 6,982,094 B2 | 1/2006 | Sowden |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,061,236 B2 | 6/2006 | Britton |
| 7,083,578 B2 | 8/2006 | Lewkowicz |
| 7,116,252 B2 | 10/2006 | Teraguchi |
| 7,118,531 B2 | 10/2006 | Krill |
| 7,122,143 B2 | 10/2006 | Sowden et al. |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,199 B2 | 3/2007 | Leung et al. |
| 7,188,767 B2 | 3/2007 | Penuela |
| 7,194,038 B1 | 3/2007 | Inkinen |
| 7,196,495 B1 | 3/2007 | Burcham |
| 7,206,630 B2 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |

(56) References Cited

U.S. PATENT DOCUMENTS

| | | |
|---|---|---|
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,311,665 B2 | 12/2007 | Hawthorne |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,247 B2 | 6/2008 | Welch et al. |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,442,164 B2 | 10/2008 | Berrang et al. |
| 7,443,290 B2 | 10/2008 | Takiguchi |
| 7,458,887 B2 | 12/2008 | Kurosawa |
| 7,469,838 B2 | 12/2008 | Brooks et al. |
| 7,471,665 B2 | 12/2008 | Perlman |
| 7,471,992 B2 | 12/2008 | Schmidt et al. |
| 7,492,128 B2 | 2/2009 | Shen |
| 7,499,674 B2 | 3/2009 | Salokannel |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,527,807 B2 | 5/2009 | Choi et al. |
| 7,537,590 B2 | 5/2009 | Santini, Jr. et al. |
| 7,539,533 B2 | 5/2009 | Tran |
| 7,542,878 B2 | 6/2009 | Nanikashvili |
| 7,547,278 B2 | 6/2009 | Miyazaki et al. |
| 7,551,590 B2 | 6/2009 | Haller |
| 7,554,452 B2 | 6/2009 | Cole |
| 7,558,620 B2 | 7/2009 | Ishibashi |
| 7,575,005 B2 | 8/2009 | Mumford |
| 7,616,111 B2 | 11/2009 | Covannon |
| 7,617,001 B2 | 11/2009 | Penner et al. |
| 7,626,387 B2 | 12/2009 | Adachi |
| 7,639,473 B2 | 12/2009 | Hsu et al. |
| 7,640,802 B2 | 1/2010 | King et al. |
| 7,645,262 B2 | 1/2010 | Greenberg et al. |
| 7,647,090 B1 | 1/2010 | Frisch et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |
| 7,673,679 B2 | 3/2010 | Harrison et al. |
| 7,678,043 B2 | 3/2010 | Gilad |
| 7,686,839 B2 | 3/2010 | Parker |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,756,587 B2 | 7/2010 | Penner et al. |
| 7,760,104 B2 | 7/2010 | Asp |
| 7,782,991 B2 | 8/2010 | Sobchak et al. |
| 7,796,043 B2 | 9/2010 | Euliano et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 7,881,799 B2 | 2/2011 | Greenberg et al. |
| 7,975,587 B2 | 7/2011 | Schneider |
| 7,978,064 B2 | 7/2011 | Zdeblick et al. |
| 7,983,189 B2 | 7/2011 | Bugenhagen |
| 8,036,731 B2 | 10/2011 | Kimchy et al. |
| 8,036,748 B2 | 10/2011 | Zdeblick et al. |
| 8,054,047 B2 | 11/2011 | Chen et al. |
| 8,054,140 B2 | 11/2011 | Fleming et al. |
| 8,055,334 B2 | 11/2011 | Savage et al. |
| 8,082,919 B2 | 12/2011 | Brunnberg et al. |
| 8,119,045 B2 | 2/2012 | Schmidt et al. |
| 8,131,376 B1 | 3/2012 | Faraji et al. |
| 8,177,611 B2 | 5/2012 | Kang |
| 8,185,191 B1 | 5/2012 | Shapiro et al. |
| 8,185,646 B2 | 5/2012 | Headley |
| 8,200,320 B2 | 6/2012 | Kovacs |
| 8,207,731 B2 | 6/2012 | Moskalenko |
| 8,224,596 B2 | 7/2012 | Agrawal et al. |
| 8,253,586 B1 | 8/2012 | Matak |
| 8,254,853 B2 | 8/2012 | Rofougaran |
| 8,271,146 B2 | 9/2012 | Heber et al. |
| 8,298,574 B2 | 10/2012 | Tsabari et al. |
| 8,343,068 B2 | 1/2013 | Najafi et al. |
| 8,374,698 B2 | 2/2013 | Ok et al. |
| 8,389,003 B2 | 3/2013 | Mintchev et al. |
| 8,404,275 B2 | 3/2013 | Habboushe |
| 8,425,492 B2 | 4/2013 | Herbert et al. |
| 8,443,214 B2 | 5/2013 | Lee et al. |
| 8,454,528 B2 | 6/2013 | Yuen et al. |
| 8,532,776 B2 | 9/2013 | Greenberg et al. |
| 8,540,664 B2 | 9/2013 | Robertson et al. |
| 8,547,248 B2 | 10/2013 | Zdeblick et al. |
| 8,558,563 B2 | 10/2013 | Zdeblick |
| 8,564,432 B2 | 10/2013 | Covannon et al. |
| 8,597,186 B2 | 12/2013 | Hafezi et al. |
| 8,634,838 B2 | 1/2014 | Hellwig et al. |
| 8,660,645 B2 | 2/2014 | Stevenson et al. |
| 8,666,687 B2 | 3/2014 | Kaneko |
| 8,668,643 B2 | 3/2014 | Kinast |
| 8,685,451 B2 | 4/2014 | Toneguzzo et al. |
| 8,698,006 B2 | 4/2014 | Bealka et al. |
| 8,758,237 B2 | 6/2014 | Sherman et al. |
| 8,784,308 B2 | 7/2014 | Duck et al. |
| 8,802,183 B2 | 8/2014 | Frank et al. |
| 8,816,847 B2 | 8/2014 | Zdeblick et al. |
| 8,836,513 B2 | 9/2014 | Hafezi et al. |
| 8,838,217 B2 | 9/2014 | Myr |
| 8,858,432 B2 | 10/2014 | Robertson |
| 8,908,943 B2 | 12/2014 | Berry et al. |
| 8,912,908 B2 | 12/2014 | Berkman et al. |
| 8,926,509 B2 | 1/2015 | Magar et al. |
| 8,932,221 B2 | 1/2015 | Colliou et al. |
| 8,945,005 B2 | 2/2015 | Hafezi et al. |
| 8,951,234 B2 | 2/2015 | Hafezi et al. |
| 8,989,837 B2 | 3/2015 | Weinstein et al. |
| 9,031,658 B2 | 5/2015 | Chiao et al. |
| 9,088,168 B2 | 7/2015 | Mach et al. |
| 9,107,806 B2 | 8/2015 | Hafezi et al. |
| 9,119,918 B2 | 9/2015 | Robertson et al. |
| 9,158,890 B2 | 10/2015 | Meredith et al. |
| 9,189,941 B2 | 11/2015 | Eschelman et al. |

(56) References Cited

U.S. PATENT DOCUMENTS

| | | |
|---|---|---|
| 9,226,663 B2 | 1/2016 | Fei |
| 9,226,679 B2 | 1/2016 | Balda |
| 9,268,909 B2 | 2/2016 | Jani et al. |
| 9,270,025 B2 | 2/2016 | Robertson et al. |
| 9,271,897 B2 | 3/2016 | Costello et al. |
| 9,277,864 B2 | 3/2016 | Yang et al. |
| 9,415,010 B2 | 8/2016 | Hafezi et al. |
| 9,433,371 B2 | 9/2016 | Hafezi et al. |
| 9,439,599 B2 | 9/2016 | Thompson et al. |
| 9,517,012 B2 | 12/2016 | Lane et al. |
| 9,599,679 B2 | 3/2017 | Taylor et al. |
| 9,649,066 B2 | 5/2017 | Zdeblick et al. |
| 9,681,842 B2 | 6/2017 | Zdeblick et al. |
| 9,741,975 B2 | 8/2017 | Laulicht et al. |
| 9,756,874 B2 | 9/2017 | Arne et al. |
| 9,968,284 B2 | 5/2018 | Vidalis et al. |
| 10,441,194 B2 | 10/2019 | Robertson et al. |
| 10,517,506 B2 | 12/2019 | Robertson et al. |
| 10,797,758 B2 | 10/2020 | Shirvani et al. |
| 2001/0027331 A1 | 10/2001 | Thompson |
| 2001/0044588 A1 | 11/2001 | Mault |
| 2001/0051766 A1 | 12/2001 | Gazdinski |
| 2002/0002326 A1 | 1/2002 | Causey et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0099423 A1 | 7/2002 | Berg et al. |
| 2002/0103425 A1 | 8/2002 | Mault |
| 2002/0128934 A1 | 9/2002 | Shaer |
| 2002/0132226 A1 | 9/2002 | Nair |
| 2002/0136744 A1* | 9/2002 | McGlynn ............ A61K 9/2009 424/400 |
| 2002/0161354 A1 | 10/2002 | Christiansen et al. |
| 2002/0179921 A1 | 12/2002 | Cohn |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0015672 A1 | 1/2003 | Gallagher |
| 2003/0017826 A1 | 1/2003 | Fishman et al. |
| 2003/0023150 A1 | 1/2003 | Yokoi et al. |
| 2003/0028226 A1 | 2/2003 | Thompson |
| 2003/0040685 A1* | 2/2003 | Lewkowicz ........ A61B 5/14539 600/593 |
| 2003/0062551 A1 | 4/2003 | Chen et al. |
| 2003/0065536 A1 | 4/2003 | Hansen |
| 2003/0076179 A1 | 4/2003 | Branch et al. |
| 2003/0083559 A1 | 5/2003 | Thompson |
| 2003/0091625 A1 | 5/2003 | Hariharan et al. |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0219484 A1 | 11/2003 | Sowden et al. |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115507 A1 | 6/2004 | Potter et al. |
| 2004/0115517 A1 | 6/2004 | Fukada et al. |
| 2004/0117062 A1 | 6/2004 | Bonney et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167465 A1 | 8/2004 | Mihai et al. |
| 2004/0167801 A1 | 8/2004 | Say et al. |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0259899 A1 | 12/2004 | Sanghvi et al. |
| 2004/0260154 A1 | 12/2004 | Sidelnik |
| 2005/0003074 A1 | 1/2005 | Brown et al. |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0063906 A1* | 3/2005 | Kraizer ................ A61B 5/073 424/9.1 |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | Delmain et al. |
| 2005/0208251 A1 | 9/2005 | Aisenbrey |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |

(56) References Cited

U.S. PATENT DOCUMENTS

| | | |
|---|---|---|
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0279054 A1 | 12/2005 | Mauze et al. |
| 2005/0280539 A1 | 12/2005 | Pettus |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0073204 A1* | 4/2006 | Goyal ................ A61K 9/284 424/471 |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0111777 A1* | 5/2006 | Chen .................... A61F 2/12 623/8 |
| 2006/0122474 A1 | 6/2006 | Teller et al. |
| 2006/0122494 A1 | 6/2006 | Bouchoucha |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0212096 A1 | 9/2006 | Stevenson |
| 2006/0216603 A1 | 9/2006 | Choi |
| 2006/0218011 A1 | 9/2006 | Walker |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0025739 A1 | 2/2007 | Moore et al. |
| 2007/0027386 A1 | 2/2007 | Such |
| 2007/0027388 A1 | 2/2007 | Chou |
| 2007/0029195 A1 | 2/2007 | Li et al. |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0114140 A1 | 5/2007 | Portier |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0000804 A1 | 1/2008 | Carey et al. |
| 2008/0014866 A1 | 1/2008 | Lipowshi |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0058614 A1 | 3/2008 | Banet |
| 2008/0062856 A1 | 3/2008 | Feher |
| 2008/0063703 A1 | 3/2008 | Gross et al. |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0117968 A1 | 5/2008 | Wang |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0240325 A1 | 10/2008 | Agazzi et al. |

(56) References Cited

U.S. PATENT DOCUMENTS

| | | |
|---|---|---|
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1 | 1/2009 | Nunez et al. |
| 2009/0010321 A1 | 1/2009 | Chalopin et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0047357 A1 | 2/2009 | Tomohira et al. |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0069724 A1 | 3/2009 | Otto et al. |
| 2009/0076343 A1 | 3/2009 | James |
| 2009/0076350 A1 | 3/2009 | Bly et al. |
| 2009/0082645 A1 | 3/2009 | Hafezi et al. |
| 2009/0087483 A1 | 4/2009 | Sison |
| 2009/0088618 A1 | 4/2009 | Ameson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0124965 A1 | 5/2009 | Greenberg et al. |
| 2009/0131774 A1 | 5/2009 | Sweitzer |
| 2009/0135886 A1 | 5/2009 | Robertson et al. |
| 2009/0142853 A1 | 6/2009 | Warrington et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0171420 A1 | 7/2009 | Brown et al. |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0194747 A1 | 8/2009 | Zou et al. |
| 2009/0197068 A1 | 8/2009 | Yamaguchi et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0260212 A1 | 10/2009 | Schmett et al. |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0287109 A1 | 11/2009 | Ferren et al. |
| 2009/0295548 A1 | 12/2009 | Ronkka |
| 2009/0296677 A1 | 12/2009 | Mahany |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0010330 A1 | 1/2010 | Rankers |
| 2010/0019848 A1 | 1/2010 | Rossi |
| 2010/0033324 A1 | 2/2010 | Shimizu et al. |
| 2010/0036269 A1 | 2/2010 | Ferren et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |

(56) References Cited

U.S. PATENT DOCUMENTS

| | | |
|---|---|---|
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0130837 A1 | 5/2010 | Matott |
| 2010/0139672 A1 | 6/2010 | Kroll et al. |
| 2010/0168659 A1 | 7/2010 | Say et al. |
| 2010/0179398 A1 | 7/2010 | Say et al. |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0297640 A1 | 11/2010 | Kumar et al. |
| 2010/0298650 A1 | 11/2010 | Moon et al. |
| 2010/0298668 A1 | 11/2010 | Hafezi et al. |
| 2010/0298730 A1 | 11/2010 | Tarassenko et al. |
| 2010/0312188 A1 | 12/2010 | Robertson et al. |
| 2010/0312580 A1 | 12/2010 | Tarassenko et al. |
| 2011/0009715 A1 | 1/2011 | O'Reilly et al. |
| 2011/0054265 A1* | 3/2011 | Hafezi .......... A61B 5/0031 600/300 |
| 2011/0065983 A1 | 3/2011 | Hafezi et al. |
| 2011/0077660 A1 | 3/2011 | Janik et al. |
| 2011/0082356 A1 | 4/2011 | Yang et al. |
| 2011/0105864 A1 | 5/2011 | Robertson et al. |
| 2011/0124983 A1 | 5/2011 | Kroll et al. |
| 2011/0134906 A1 | 6/2011 | Garudadri et al. |
| 2011/0160549 A1 | 6/2011 | Saroka et al. |
| 2011/0224912 A1 | 9/2011 | Bhavaraju et al. |
| 2011/0230732 A1 | 9/2011 | Edman et al. |
| 2011/0243483 A1 | 10/2011 | Crump et al. |
| 2011/0270135 A1 | 11/2011 | Dooley et al. |
| 2012/0004520 A1 | 1/2012 | Whitworth et al. |
| 2012/0011699 A1 | 1/2012 | Hafezi et al. |
| 2012/0016005 A1* | 1/2012 | Samarsky .......... A61K 47/62 514/44 A |
| 2012/0016231 A1 | 1/2012 | Westmoreland |
| 2012/0032816 A1 | 2/2012 | Cho et al. |
| 2012/0059257 A1 | 3/2012 | Duck et al. |
| 2012/0062371 A1 | 3/2012 | Radivojevic et al. |
| 2012/0071743 A1 | 3/2012 | Todorov et al. |
| 2012/0109112 A1 | 5/2012 | Strand et al. |
| 2012/0179004 A1 | 7/2012 | Roesicke et al. |
| 2012/0189589 A1* | 7/2012 | Van Epps .......... A61K 9/06 424/93.7 |
| 2012/0191123 A1* | 7/2012 | Brister .......... A61F 5/0043 606/191 |
| 2012/0244221 A1* | 9/2012 | Dill .......... A61K 31/122 424/484 |
| 2012/0245043 A1 | 9/2012 | England |
| 2012/0276451 A1 | 11/2012 | Lestriez et al. |
| 2012/0299723 A1 | 11/2012 | Hafezi et al. |
| 2013/0030366 A1 | 1/2013 | Robertson et al. |
| 2013/0129869 A1 | 5/2013 | Hafezi et al. |
| 2013/0129872 A1 | 5/2013 | Kruger |
| 2013/0131283 A1 | 5/2013 | Wang et al. |
| 2013/0144132 A1 | 6/2013 | Hafezi et al. |
| 2013/0171596 A1 | 7/2013 | French |
| 2013/0172690 A1 | 7/2013 | Arne et al. |
| 2013/0185228 A1 | 7/2013 | Dresner |
| 2013/0196012 A1 | 8/2013 | Dill |
| 2013/0199662 A1 | 8/2013 | Gebbink |
| 2013/0209877 A1 | 8/2013 | Kren et al. |
| 2013/0223028 A1 | 8/2013 | Arne et al. |
| 2013/0244002 A1 | 9/2013 | Sanofi |
| 2013/0275296 A1 | 10/2013 | Tietzen et al. |
| 2013/0328416 A1 | 12/2013 | Whitworth et al. |
| 2014/0009262 A1 | 1/2014 | Robertson et al. |
| 2014/0066734 A1 | 3/2014 | Zdeblick |
| 2014/0179221 A1 | 6/2014 | Whitworth et al. |
| 2014/0180202 A1 | 6/2014 | Zdeblick et al. |
| 2014/0280125 A1 | 9/2014 | Bhardwaj et al. |
| 2014/0308930 A1 | 10/2014 | Tran |
| 2014/0349256 A1 | 11/2014 | Connor |
| 2014/0374276 A1 | 12/2014 | Guthrie et al. |
| 2015/0017486 A1 | 1/2015 | Lai |
| 2015/0059922 A1 | 3/2015 | Thompson et al. |
| 2015/0080677 A1 | 3/2015 | Thompson et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0080681 A1 | 3/2015 | Hafezi et al. |
| 2015/0112243 A1 | 4/2015 | Hafezi et al. |
| 2015/0127737 A1 | 5/2015 | Thompson et al. |
| 2015/0127738 A1 | 5/2015 | Thompson et al. |
| 2015/0149375 A1 | 5/2015 | Thompson et al. |
| 2015/0150480 A1 | 6/2015 | Zdeblick et al. |
| 2015/0164746 A1 | 6/2015 | Costello et al. |
| 2015/0173646 A1 | 6/2015 | Berkman et al. |
| 2015/0223751 A1 | 8/2015 | Zdeblick et al. |
| 2015/0230729 A1 | 8/2015 | Zdeblick et al. |
| 2015/0248833 A1 | 9/2015 | Arne et al. |
| 2015/0352343 A1 | 12/2015 | Hafezi et al. |
| 2016/0033667 A1 | 2/2016 | Schmidt et al. |
| 2016/0345906 A1 | 12/2016 | Johnson et al. |
| 2016/0380708 A1 | 12/2016 | Dua et al. |
| 2017/0000179 A1 | 1/2017 | Cheng et al. |
| 2017/0014046 A1 | 1/2017 | Hafezi et al. |
| 2017/0020182 A1 | 1/2017 | Schmidt et al. |
| 2017/0216569 A1 | 8/2017 | Hafezi et al. |
| 2017/0265813 A1 | 9/2017 | Zdeblick et al. |
| 2017/0274194 A1 | 9/2017 | Robertson et al. |
| 2017/0296799 A1 | 10/2017 | Hafezi et al. |
| 2018/0026680 A1 | 1/2018 | Shirvani et al. |
| 2018/0110441 A1 | 4/2018 | Frank et al. |
| 2018/0184698 A1 | 7/2018 | Arne et al. |
| 2018/0214048 A1 | 8/2018 | Zdeblick et al. |
| 2018/0229996 A1 | 8/2018 | Thompson |
| 2019/0191006 A1 | 6/2019 | Thompson et al. |

FOREIGN PATENT DOCUMENTS

| | | |
|---|---|---|
| CN | 101287411 A | 10/2008 |
| CN | 101795202 | 8/2010 |
| DE | 10313005 | 10/2004 |
| DE | 102005007576 A | 8/2006 |
| EP | 0344939 | 12/1989 |
| EP | 0526166 | 2/1993 |
| EP | 0981152 | 2/2000 |
| EP | 1246356 | 10/2002 |
| EP | 1534054 | 5/2005 |
| EP | 1702553 | 9/2006 |
| EP | 1244308 | 12/2007 |
| EP | 2143369 | 1/2010 |
| GB | 827762 | 2/1960 |
| GB | 2419110 A | 4/2006 |
| JP | 61072712 | 4/1986 |
| JP | H01285247 | 11/1989 |

(56) References Cited

FOREIGN PATENT DOCUMENTS

| | | |
|---|---|---|
| JP | 05-228128 | 9/1993 |
| JP | H11195415 | 7/1999 |
| JP | 2000-506410 | 5/2000 |
| JP | 2002263185 | 9/2002 |
| JP | 2002282219 | 10/2002 |
| JP | 2003050867 | 2/2003 |
| JP | 2004-313242 | 11/2004 |
| JP | 2005-073886 | 3/2005 |
| JP | 2005-087552 | 4/2005 |
| JP | 2005-304880 | 4/2005 |
| JP | 2005102959 | 4/2005 |
| JP | 2005124708 | 5/2005 |
| JP | 2005514966 | 5/2005 |
| JP | 2005343515 | 12/2005 |
| JP | 20055332328 | 12/2005 |
| JP | 2006006377 | 1/2006 |
| JP | 2006509574 | 3/2006 |
| JP | 2007200739 | 8/2007 |
| JP | 2007-313340 | 12/2007 |
| JP | 2009514870 | 4/2009 |
| JP | 2009528909 | 8/2009 |
| KR | 2006077523 | 7/2006 |
| TW | 200406192 | 5/2004 |
| TW | 200916136 | 4/2009 |
| TW | 201231091 A1 | 8/2012 |
| WO | WO1988002237 | 4/1988 |
| WO | WO1992021307 | 12/1992 |
| WO | WO1993008734 | 5/1993 |
| WO | WO1993019667 | 10/1993 |
| WO | WO1994001165 | 1/1994 |
| WO | WO1997039963 | 10/1997 |
| WO | WO1998043537 | 10/1998 |
| WO | WO1999037290 | 7/1999 |
| WO | WO1999059465 | 11/1999 |
| WO | WO2000032474 | 6/2000 |
| WO | WO2000033246 | 6/2000 |
| WO | WO2001047466 | 7/2001 |
| WO | WO2001058236 | 8/2001 |
| WO | WO2001074011 | 10/2001 |
| WO | WO2001080731 | 11/2001 |
| WO | WO2002000920 | 1/2002 |
| WO | WO2002045489 | 6/2002 |
| WO | WO2002058330 | 7/2002 |
| WO | WO2002062276 | 8/2002 |
| WO | WO2002087681 | 11/2002 |
| WO | WO2002095351 | 11/2002 |
| WO | WO2003005877 | 1/2003 |
| WO | WO2003050643 | 6/2003 |
| WO | WO2003068061 | 8/2003 |
| WO | WO2004014225 | 2/2004 |
| WO | WO2004019172 | 3/2004 |
| WO | WO2004039256 | 5/2004 |
| WO | WO2004066833 | 8/2004 |
| WO | WO2004066834 | 8/2004 |
| WO | WO2004066903 | 8/2004 |
| WO | WO2004068881 | 8/2004 |
| WO | WO2004075032 | 9/2004 |
| WO | WO2004109316 | 12/2004 |
| WO | WO2005011237 | 2/2005 |
| WO | WO2005020023 | 3/2005 |
| WO | WO2005024687 | 3/2005 |
| WO | WO2005041438 | 5/2005 |
| WO | WO2005047837 | 5/2005 |
| WO | WO2005051166 | 6/2005 |
| WO | WO2005053517 | 6/2005 |
| WO | WO2005083621 | 9/2005 |
| WO | 2005105053 A2 | 11/2005 |
| WO | WO2005110238 | 11/2005 |
| WO | WO2005123569 | 12/2005 |
| WO | WO2006021932 | 3/2006 |
| WO | WO2006027586 | 3/2006 |
| WO | WO2006028347 | 3/2006 |
| WO | WO2006055892 | 5/2006 |
| WO | WO2006055956 | 5/2006 |
| WO | WO2006075016 | 7/2006 |
| WO | 2006087288 A1 | 8/2006 |
| WO | WO2006100620 | 9/2006 |
| WO | WO2006104843 | 10/2006 |
| WO | WO2006116718 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007127316 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2008008281 | 1/2008 |
| WO | WO2008012700 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009000447 | 12/2008 |
| WO | WO2009001108 | 12/2008 |
| WO | WO2009006615 | 1/2009 |
| WO | WO2009029453 | 3/2009 |
| WO | WO2009031149 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | 2009106952 A1 | 9/2009 |
| WO | WO2009111664 | 9/2009 |
| WO | WO2009146082 | 12/2009 |
| WO | WO2001000085 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010080765 | 7/2010 |
| WO | WO2010080843 | 7/2010 |
| WO | WO2010107563 | 9/2010 |
| WO | WO2010129288 | 11/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012112561 | 8/2012 |

(56) References Cited

FOREIGN PATENT DOCUMENTS

| WO | WO2015112603 | 7/2015 |
|---|---|---|
| WO | WO2015112604 | 7/2015 |
| WO | 2018018034 A1 | 1/2018 |

OTHER PUBLICATIONS

International Search Report for PCT/US2014/013382, dated May 26, 2014 (3 pages).
AADE, "AADE 37th Annual Meeting San Antonio Aug. 4-7, 2010" American Association of Diabetes Educators (2010); http://www.diabeteseducator.org/annualmeeting/2010/index.html; 2 pp.
Arshak et al., A Review and Adaptation of Methods of Object Tracking to Telemetry Capsules IC-Med (2007) vol. 1, No. 1, Issue 1, 12pp.
"ASGE Technology Status Evaluation Report: wireless capsule endoscopy" American Soc. For Gastrointestinal Endoscopy (2006) vol. 63, No. 4; 7 pp.
Aydin et al., "Design and implementation considerations for an advanced wireless interface in miniaturized integrated sensor Microsystems" Sch. of Eng. & Electron., Edinburgh Univ., UK; (2003); abstract.
Barrie, Heidelberg pH capsule gastric analysis. Texbook of Natural Medicine, (1992), Pizzorno, Murray & Barrie.
Bohidar et al., "Dielectric Behavior of Gelatin Solutions and Gels" Colloid Polym Sci (1998) 276:81-86.
Brock, "Smart Medicine: The Application of Auto-ID Technology to Healthcare" Auto-ID Labs (2002) http://www.autoidlabs.org/uploads/media/MIT-AUTOID-WH-010.pdf.
Carlson et al., "Evaluation of a non-invasive respiratory monitoring system for sleeping subjects" Physiological Measurement (1999) 20(1): 53.
Coury, L. "Conductance Measurement Part 1: Theory"; Current Separations, 18:3 (1999) p. 91-96.
Delvaux et al., "Capsule endoscopy: Technique and indications" Clinical Gastroenterology (2008) vol. 22, Issue 5, pp. 813-837.
Description of ePatch Technology Platform for ECG and EMG, located it http://www.madebydelta.com/imported/images/DELTA_Web/documents/ME/ePatch_ECG_EMG.pdf, Dated Sep. 2, 2010.
Dhar et al., "Electroless nickel plated contacts on porous silicon" Appl. Phys. Lett. 68 (10) pp. 1392-1393 (1996).
Eldek A., "Design of double dipole antenna with enhanced usable bandwidth for wideband phased array applications" Progress in Electromagnetics Research PIER 59, 1-15 (2006).
Fawaz et al., "Enhanced Telemetry System using CP-QPSK Band-Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.
Ferguson et al., "Dielectric Constant Studies III Aqueous Gelatin Solutions" J. Chem. Phys. 2, 94 (1934) p. 94-98.
Furse C. M., "Dipole Antennas" J. Webster (ed). Wiley Encyclopedia of Electrical and Electronics Engineering (1999) p. 575-581.
Gaglani S. "Put Your Phone, Or Skin, on Vibrate" MedGadget (2012) http://medgadget.com/2012/03/put-your-phone-or-skin-on-vibrate.html 8pp.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng. (2007) 54(12): 2231-6; abstract.
Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.
Heydari et al., "Analysis of the PLL jitter due to power/ground and substrate noise"; IEEE Transactions on Circuits and Systems (2004) 51(12): 2404-16.

Hoeksma, J. "New 'smart pill' to track adherence" E-Health-Insider (2010) http://www.e-health-insider.com/news/5910/new_'smart_pill'_monitors_medicines.
Hoover et al., "Rx for health: Engineers design pill that signals it has been swallowed" University of Florida News (2010) 2pp.; http://news.ufl.edu/2010/03/31/antenna-pill-2/.
Intromedic, MicroCam Innovative Capsule Endoscope Pamphlet. (2006) 8 pp (http://www.intromedic.com/en/product/productinfo.asp).
ISFET—Ion Sensitive Field-Effect Transistor; MICROSENS S.A. pdf document. First cited by Examiner in Office Action dated Jun. 13, 2011 for U.S. Appl. No. 12/238,345; 4pp.
Jung, S. "Dissolvable 'Transient Electronics' Will Be Good For Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" (2010); http://www.artificialpancreasproject.com/; 3 pp.
Kamada K., "Electrophoretic deposition assisted by soluble anode" Materials Letters 57 (2003) 2348-2351.
Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.
Kim et al., "A Semi-Interpenetrating Network System for a Polymer Membrane"; Eur. Polym. J. vol. 33 No. 7; pp. 1009-1014 (1997).
Li, P-Y, et al. "An electrochemical intraocular drug delivery device", Sensors and Actuators A 143 (2008) p. 41-48.
Lifescan, "OneTouch UltraLink™" http://www.lifescan.com/products/meters/ultralink (2010) 2 pp.
Mackay et al., "Radio Telemetering from within the Body Inside Information is Revealed by Tiny Transmitters that can be Swallowed or Implanted in Man or Animal" Science (1991) 1196-1202; 134; American Association for the Advancement of Science, Washington D.C.
Mackay et al., "Endoradiosonde" Nature, (1957) 1239-1240, 179 Nature Publishing Group.
McKenzie et al., "Validation of a new telemetric core temperature monitor" J. Therm. Biol. (2004) 29(7-8):605-11.
Medtronic, "CareLink Therapy Management Software for Diabetes" (2010); https://carelink.minimed.com/patient/entry.jsp?bhcp=1; 1 pp.
Medtronic, "Carelink™ USB " (2008) http://www.medtronicdiabetes.com/pdf/carelink_usb_factsheet.pdf 2pp.
Medtronic "The New MiniMed Paradigm® REAL-Time Revel™ System" (2010) http://www.medtronicdiabetes.com/products/index.html; 2 pp.
Medtronic, "Mini Med Paradigm® Revel™ Insulin Pump" (2010) http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf ; 4 pp.
Melanson, "Walkers swallow RFID pills for science" Engadget (2008); http://www.engadget.com/2008/07/29/walkers-swallow-rfid-pills-for-science/.
Minimitter Co. Inc. "Actiheart" Traditional 510(k) Summary. Sep. 27, 2005.
Minimitter Co. Inc. Noninvasive technology to help your studies succeed. Mini Mitter.com Mar. 31, 2009.
Mini Mitter Co, Inc. 510(k) Premarket Notification Mini-Logger for Diagnostic Spirometer. Sep. 21, 1999.
Mini Mitter Co, Inc. 510(k) Premarket Notification for VitalSense. Apr. 22, 2004.
Minimitter Co. Inc. VitalSense Integrated Physiological Monitoring System. Product Description. (2005).
Minimitter Co. Inc. VitalSense Wireless Vital Signs Monitoring. Temperatures.com Mar. 31, 2009.
Mojaverian et al., "Estimation of gastric residence time of the Heidelberg capsule in humans: effect of varying food composition" Gastroenterology (1985) 89:(2): 392-7.

(56) References Cited

OTHER PUBLICATIONS

O'Brien et al., "The Production and Characterization of Chemically Reactive Porous Coatings of Zirconium Via Unbalanced Magnetron Sputtering" Surface and Coatings Technology (1996) 86-87; 200-206.
Park, "Medtronic to Buy MiniMed for $3.7 Billion" (2001) HomeCare; http://homecaremag.com/mag/medical_medtronic_buy_minimed/; 2 pp.
Philips Respironics Products, Noninvasive Technology to Help Your Studies Succeed. 510 (k) Permanent Notification for Vital Sense. Apr. 22, 2004; http/minimitter.com/products.cfm.
Radio Antennae, http://www.erikdeman.de/html/sail018h.htm; (2008) 5 pages.
"RFID "pill" monitors marchers" RFID News (2008) http://www.rfidnews.org/2008/07/23/rfid-pill-monitors-marchers/.
Rolison et al., "Electrically conductive oxide aerogels: new materials in electrochemistry" J. Mater. Chem. (2001) 1, 963-980.
Roulstone, et al., "Studies on Polymer Latex Films: I. A study of latex film morphology" Polymer International 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf.
Shawgo, R.S. et al. "BioMEMS from drug delivery", Current Opinion in Solid State and Material Science 6 (2002), p. 329-334.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010).
"Smartlife awarded patent for knitted transducer" Innovation in Textiles News: http://www.innovationintextiles.com/articles/208.php; 2pp. (2009).
"The SmartPill Wireless Motility Capsule" Smartpill, The Measure of GI Health; (2010) http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal Apr. 27, 2010; http://www.rfidjournal.com/article/view/7560/1 3pp.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Trutag Technologies, Inc., Spectral Microtags for Authentication and Anti-Counterfeiting; "Product Authentication and Brand Protection Solutions"; http://www.trutags.com/; downloaded Feb. 12, 2013; 1 pp.
Walkey, "MOSFET Structure and Processing"; 97.398* Physical Electronics Lecture 20; 24 pp.
Watson, et al., "Determination of the relationship between the pH and conductivity of gastric juice" Physiol Meas. 17 (1996) pp. 21-27.
Whipple, Fred L.; "Endoradiosonde," Nature, Jun. 1957, 1239-1240.
Winter, J. et al. "The material properties of gelatin gels"; USA Ballistic Research Laboratories, Mar. 1975, p. 1-157.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006.
Zimmerman, "Personal Area Networks: Near-field intrabody communication" IBM Systems Journal (1996) 35 (3-4):609-17.
Zworkin, "A Radio Pill" Nature, (1957) 898, 179 Nature Publishing Group.
Au-Yeung, K., et al., "A Networked System for Self-Management of Drug Therapy and Wellness", Wireless Health '10, Oct. 5-7, 2010, San Diego, 9 pages.
Target Innovations, Tablet Metal Detector, https ://web. arch ive. org/web/20 130215063351/http://www. metaldetectorindia.com/tablet-metal-detector. html, Feb. 15, 2013.
TargetPharmaceutical Metal Detector, Feb. 15, 2013 downloaded from Target Innovations, Tablet Metal Detector, Feb. 15, 2013.
Youtube video Pharmaceutical Metal Detector/Tablet Metal Detector/ Capsule Metal Detector/ Dry Fruits; https://www.youtube.com/watch?v=I0126txam_s, May 12, 2012.

\* cited by examiner

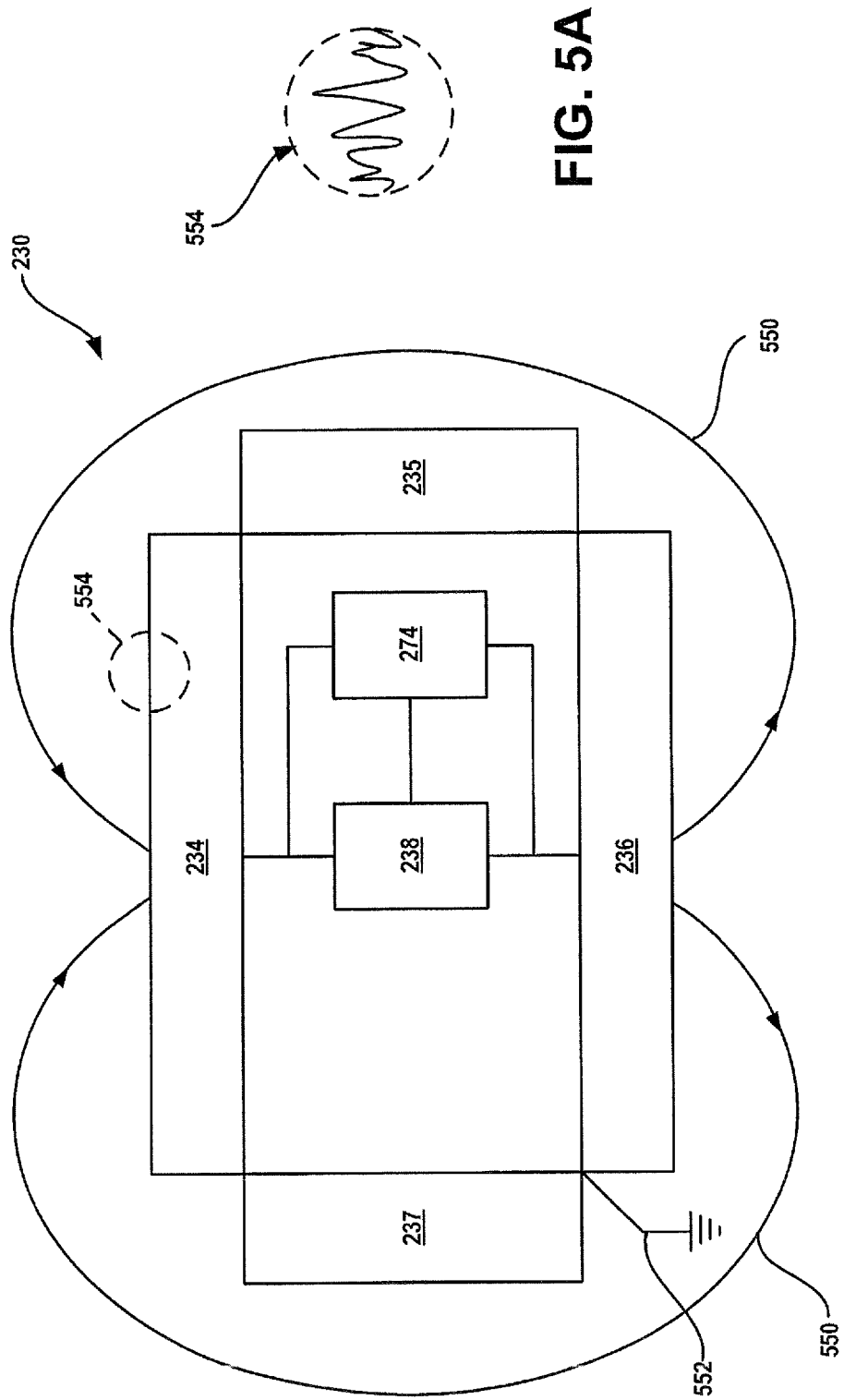

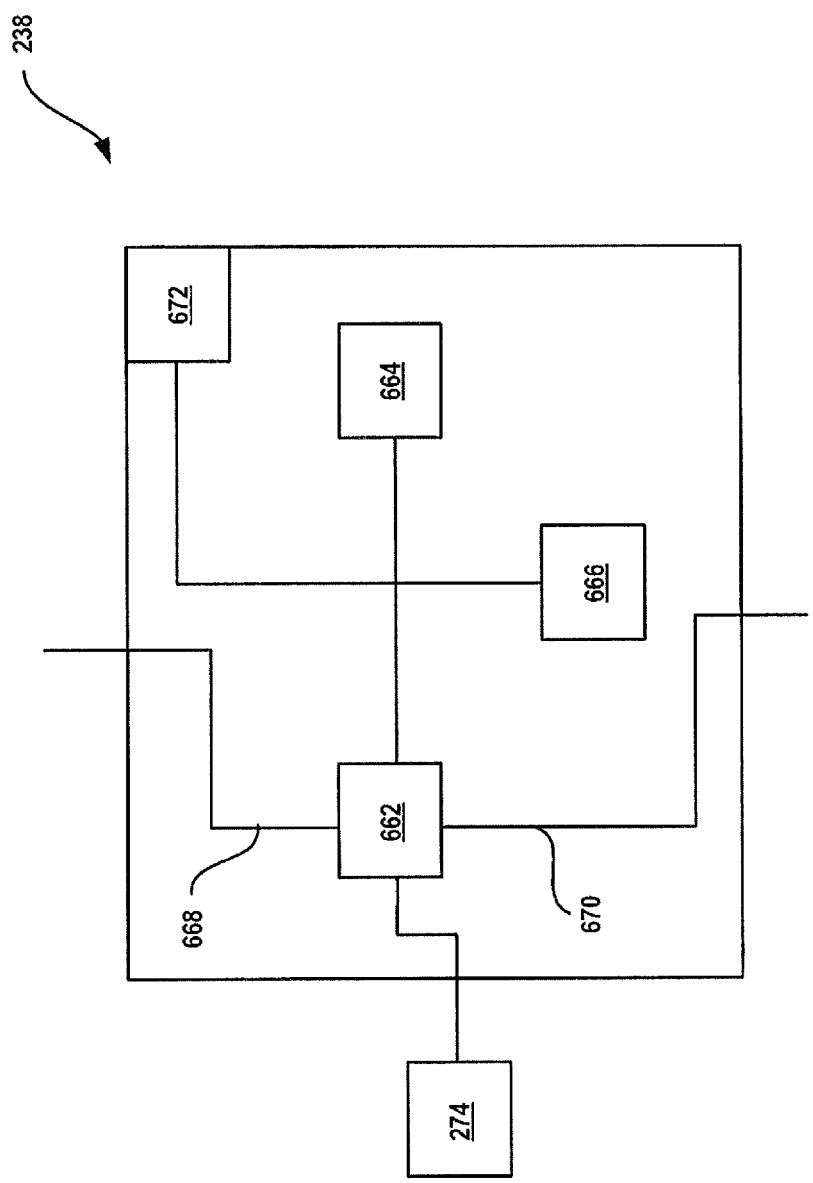

HIGHLY-SWELLABLE POLYMERIC FILMS AND COMPOSITIONS COMPRISING THE SAME

CROSS-REFERENCE TO RELATED APPLICATIONS

This application is the U.S. National Stage application filed under 35 U.S.C. § 371(c) of International Application No. PCT/US2014/013382, filed on Jan. 28, 2014, which claims the benefit, under 35 USC § 119(e), of U.S. Provisional Patent Application Ser. No. 61/758,030 filed Jan. 29, 2013; the entirety of both applications are incorporated by reference.

INTRODUCTION

A variety of different ingestible compositions have been developed for nutritional, therapeutic and non-therapeutic uses. Examples of different types of ingestible compositions include orally ingestible tablets, capsules and liquids. A given orally ingestible formulation may include a variety of different components, such as active agents, carrier materials (including binders, bulking agents and other excipients), flavoring agents, coloring agents, etc. More recently, ingestible compositions which include a device component, such as an RFID tag or an ingestible event marker, have been developed.

As with many consumer products, ingestible compositions are not manufactured at the time of and location of use. Instead, they are generally manufactured at one or more fabrication facilities, stored for a period of time and then shipped to the end-user. Upon receipt, the end-user may further store them for a period of time before use.

During the multiple storage periods, and even manufacturing periods, such as mentioned above, the quality of the ingestible composition, e.g., in terms of effectiveness, may be degraded in some way. For example, exposure to humidity, elevated temperatures, microorganisms and oxidizing agents, as well other environmental hazards, can negatively impact the quality of the ingestible composition.

SUMMARY

Highly-swellable polymeric films are provided. Aspects also include ingestible compositions that include the highly-swellable polymeric film and an ingestible component. Aspects further include methods of making and using the compositions.

Aspects of the invention are referred to in the following clauses:

1. A highly-swellable polymeric film that rapidly swells without disintegrating upon contact with an aqueous medium.
2. The highly-swellable polymeric film according to Clause 1, wherein the film rapidly swells to 10 times or greater in volume upon contact with an aqueous medium, preferably wherein the film swells to 10 times or greater in volume within 1 minute or less upon contact with an aqueous medium.
3. The highly-swellable polymeric film according to any of the preceding clauses wherein the film is configured to absorb 10 g or more of water per gram of film upon contact with an aqueous medium.
4. The highly-swellable polymeric film according to any of the preceding clauses wherein the film comprises one or more of the following; an ionic polymer, an anionic polymer, cationic polymer.
5. The highly-swellable polymeric film according to clause 4 wherein the ionic polymer comprises monomeric units having an acidic functional group, such as a carboxyl, sulfate, sulfonate, phosphate or phosphonate group, or a basic functional group, such as an amino, substituted amino or guanidyl group.
6. The highly-swellable polymeric film according to clause 4 or 5 wherein the anionic polymer is formed from the ionic polymer in an aqueous solution at a suitable pH range, e.g., 7 to 14 pH.
7. The highly-swellable polymeric film according to any of the clauses 4-6 wherein the cationic polymer is formed from the ionic polymer in an aqueous solution at a suitable pH range, e.g., 1 to 7 pH.
8. The highly-swellable polymeric film according to any of the clauses 4-7 wherein anionic polymers are chosen from the group comprising polysaccharide polymers for example alginates, e.g., alginic acid and salts thereof e.g., sodium alginate, calcium alginate, potassium alginate, which alginates may be cross linked, polyacrylic acid, dextran sulfate, carboxymethylcellulose, hyaluronic acid, polyglucuronic acid, polymanuronic acid, polygalacturonic acid, polyarabinic acid; chrondroitin sulfate and dextran phosphate.
9. The highly-swellable polymeric film according to any of the clauses 4-8 wherein cationic polymers are chosen from the group comprising chitosan, polyethylenimine, poly-L-lysine, and dimethylaminodextran.
10. The highly-swellable polymeric film according to any of the preceding clauses further comprising a polyacrylic acid.
11. The highly-swellable polymeric film according to clause 10 wherein the polyacrylic acid is chosen from the group comprising homopolymeric polyacrylic acid, copolymers, including both random and block copolymers, of acrylic acid residues and one or more non-acrylic acid residues, e.g., acrylate residues.
12. The highly-swellable polymeric film according to clauses 10 or 11 wherein the polyacrylic acid is cross-linked.
13. The highly-swellable polymeric film according to clause 12 wherein the dry weight ratio of the two types of polymers in the film may vary, and in some instances ranges from 25 to 95%, such as 50 to 80% and including 70 to 80% alginate.
14. The highly-swellable polymeric film according to any of the preceding clauses further comprising a conductivity enhancing agent, for example a porogen.
15. The highly-swellable polymeric film according to any of the preceding clauses having pores therein ranging in some instances from 1 to 1000 µm, such as 1 to 500 µm and including 1 to 250 µm.
16. The highly-swellable polymeric film according to clauses 14 or 15 comprising one or more porogens selected from both inorganic and organic porogens, for example inorganic salts, e.g., NaCl, $MgCl_2$, $CaCl_2$, $NH_4Cl$, $NH_4PO_4$, $NH_4CO_3$; soluble biocompatible salts; sugars (e.g., sugar alcohols), polysaccharides (e.g., dextran (poly(dextrose)), water soluble small molecules, natural or synthetic polymers, oligomers, or monomers that are water soluble or degrade quickly under physiological conditions, including but not limited to: polyethylene glycol, polyvinyl alcohol, poly(vinylpyrollidone), pullulan, poly(glycolide), poly(lactide), poly(lactide-co-glycolide), other polyesters, and starches.
17. The highly-swellable polymeric film according to any of the clauses 14-16 wherein the amount of porogen component ranges from 1 to 40, including from 5 to 10 dry weight percent of the film.

18. The highly-swellable polymeric film according to any of the preceding clauses further comprising a binding agent, preferably selected from the group comprising celluloses, e.g., methyl cellulose, hydroxymethyl cellulose, hydroxyethyl cellulose, hydroxypropyl cellulose, hydroxypropyl methylcellulose, etc.; polyvinyl pyrrolidone; polyethylene oxides; gums, acrylate polymers; methacrylate polymers; copovidone.

19. The highly-swellable polymeric film according to clause 18 wherein the amount of binding agent is present in amount ranging from 1 to 50, such as 5 to 10 dry weight percent of the film.

20. The highly-swellable polymeric film according to any of the preceding clauses further comprising a plasticizing agent, preferably selected from the group comprising fatty acids, e.g., oleic acid, palmitic acid, etc.; dioctylphtalate; phospholipid; phosphatidic acid; polyethylene glycol; glycerine; butylhydroxytoluene; salts; saccharides, e.g., sucrose.

21. The highly-swellable polymeric film according to clause 20 wherein the amount of plasticizing agent ranges from 0.01 to 10, including from 2 to 5 dry weight percent of the film.

22. The highly-swellable polymeric polymeric film according to any of the preceding clauses being non-toxic and ingestible.

23. The highly-swellable polymeric film according to any of the preceding clauses which does not swell substantially upon contact with a gaseous medium, for example water vapour.

24. The highly-swellable polymeric film according to any of the preceding clauses comprising a mixture of sodium alginate and cross linked polyacrylic acid.

25. The highly-swellable polymeric film according to any of the preceding clauses which conducts electricity when swollen, and/or is swellable without disintegrating.

26. Use of a polymeric film according to any of the preceding clauses as a moisture protective coating for an electrical element, for example a battery and/or an ingestible event marker 27. An assembly for ingestion, comprising an ingestible component and a highly-swellable polymeric film according to any of the clauses 1-25 associated therewith.

28. Assembly according to clause 27 wherein the ingestible component is completely or partially coated with the highly-swellable polymeric film.

29. Assembly according to clauses 27 or 28 wherein the ingestible component comprises a pharmaceutically active component.

30. Assembly according to any of the clauses 27-29 wherein the ingestible component comprises an electronic unit and/or a mechanical unit, which electronic unit can comprise electronic circuitry, and is preferably an ingestible event marker.

31. Assembly according to clause 30 wherein the ingestible event marker comprises identifier circuitry and a current path extender.

32. Assembly according to clause 31 wherein the current path extender comprises a highly-swellable polymeric film according to any of the preceding clauses 1-25.

33. Assembly according to any of the preceding clauses 30-32 wherein the ingestible event indicator comprises:

a support;

circuitry associated with the support;

a first material electrically coupled to the circuitry and associated with the support; and a second material electrically coupled to the circuitry, wherein the second material is associated with the support and is electrically isolated from the first material;

wherein the first and second materials are selected to provide a voltage potential difference when in contact with a conducting fluid.

34. Assembly according to Clause 33, wherein the highly-swellable polymeric film covers at least a portion of one of the first material or second material.

35. Assembly according to clause 34 wherein the highly-swellable polymeric film inhibits reaction of at least one of the first material or second material with ambient moisture.

36. Assembly according to any of the clauses 33-35 wherein the highly-swellable polymeric film, when swollen, provides for conduction between at least one of the first material and the second material and an aqueous medium in which the composition is present.

37. Assembly according to any of the clauses 33-36 wherein the highly-swellable polymeric film covers at least a portion of the first material and/or the second material.

38. Assembly according to any of the clauses 33-37, wherein the second material is a salt, preferably selected from the group consisting of copper salts, iron salts and silver salts.

39. Assembly according to any of the clauses 33-38 wherein the first material comprises a metal.

40. Assembly according to Clause 39, wherein the metal is selected from the group consisting of magnesium, zinc, sodium, lithium and iron and alloys thereof.

41. Assembly according to any of the preceding clauses 33-40 wherein the highly-swellable polymeric film is associated with the support and is configured as a signal amplification that increases a length of a current path between the first and second materials.

42. The ingestible composition according to any of the preceding clauses 33-41 wherein the ingestible composition wherein the highly-swellable polymeric film is configured to separate the event indicator from the pharmaceutically active component upon swelling.

43. A system comprising:

an assembly according to any of the preceding clauses 33-42 and a receiver configured to receive a communication associated with the ingestible component.

44. Use of a system according to clause 43 for providing information when the assembly is ingested.

45. An ingestible event marker coated with a highly-swellable polymeric film according to any of the preceding clauses 1-25.

46. Use of a highly-swellable polymeric film according to any of the preceding clauses 1-25 as a moisture barrier and/or as a conductor or electricity when in a swollen state.

47. Process for providing a highly-swellable polymeric film according to any of the preceding clauses 1-25 comprising the step of blending polymeric components with a solvent.

48. Process for stably associating highly-swellable polymeric film according to any of the preceding clauses 1-25 with an ingestible event marker or ingestible component comprising one or more protocols selected from the group consisting of laminating, pressing, stamping, extruding, molding, gluing and coating.

49. The method according to Clause 48, wherein at least a portion of the method is automated.

BRIEF DESCRIPTION OF THE FIGURES

FIG. 5 shows ionic transfer or the current path through a conducting fluid when the event indicator system of an ingestible event indicator is in contact with conducting liquid and in an active state.

FIG. 5A shows an exploded view of the surface of a dissimilar material as illustrated in FIG. 5.

FIG. 6 is a block diagram illustration of one aspect of the control device used in the system of FIGS. 2 and 4.

DETAILED DESCRIPTION

Figure 1:
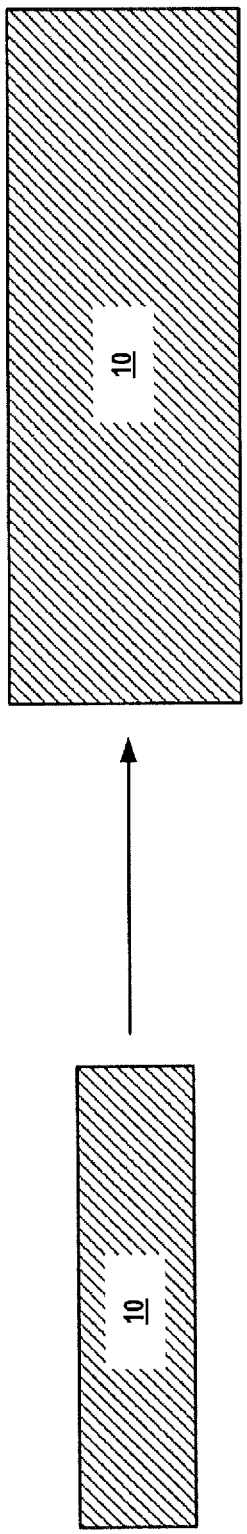
FIG. 1 is a representation of one aspect of a highly-swellable ingestible polymeric film, showing transition of the film from an unswollen to swollen state following contact with an aqueous medium and swelling.

Highly-swellable polymeric films are provided. Aspects also include ingestible compositions that include the highly-swellable polymeric film and an ingestible component. Aspects further include methods of making and using the compositions.

Compositions

As summarized above, aspects of the invention include highly-swellable ingestible polymeric films, as well as compositions which include these films in addition to other components, e.g., ingestible components such as ingestible devices; minimally dimensioned components; etc.

Highly-Swellable Polymeric Films

Aspects of the invention include highly-swellable polymeric films. As used herein, the term "film" means a thin sheet or layer. While the dimensions of the film may vary, in some instances the film has a thickness of 10 microns or greater, such as 50 microns or greater, including 100 microns or greater, and ranges in thickness in some instances from 10 to 1000, such as 20 to 200 and including 30 to 60 microns. The top and bottom surfaces of the film may have a variety of different configurations, including but not limited to rectangular, trapezoidal, triangular, etc.; curvilinear, such as circular, ovoid or other curvilinear shape, etc. Where the film has surface which may be defined by length and width, these dimensions may vary, where in some instances the length ranges from 1 to 20, such as 2 to 10 and including 3 to 6 mm and the width ranges from 1 to 20, such as 2 to 10 and including 3 to 6 mm.

Films of interest are highly-swellable. By highly-swellable is meant that that the films are able to swell substantially upon contact with a liquid aqueous medium, such that they grow substantially in bulk (i.e., magnitude in three dimensions, e.g., which may be assessed in terms of a change in volume, etc.) by the absorption of water upon contact with an aqueous medium. Where the swelling results in a change in volume of the film, the volume may increase by a factor of 10 or greater, such as a factor of 15 or greater, including a factor of 20 or greater, e.g., a factor of 25 or greater, a factor of 30 or greater, a factor of 40 or greater, including a factor of 50 or greater, such as a factor of 100 or greater, for example a factor of 500 or greater, including a factor of 1000 or greater, as compared to the initial volume prior to contact with the liquid aqueous medium. Upon swelling, the mass of film may increase as well, where in some instances the mass increases by a factor of 10 or greater, such as a factor of 15 or greater, including a factor of 20 or greater, e.g., a factor of 25 or greater, a factor of 30 or greater, a factor of 40 or greater, including a factor of 50 or greater, such as a factor of 100 or greater, for example a factor of 500 or greater, including a factor of 1000 or greater, as compared to the initial mass prior to contact with the aqueous medium.

Highly-swellable polymeric films described herein rapidly swell upon contact with a liquid aqueous medium. By "rapidly swell" is meant that upon contact with a liquid aqueous medium, the films achieve substantially maximum swelling in a short period of time. As such, following contact with an aqueous medium, the films achieve 90% or more, such as 95% percent or more maximal swelling in a period of time of 10 minutes or less, such as 5 minutes or less, including 1 minute or less. In some instances, the films swell in volume by a factor of 10 or greater, such as a factor of 15 or greater, including a factor of 20 or greater, e.g., a factor of 25 or greater, a factor of 30 or greater, a factor of 40 or greater, including a factor of 50 or greater, such as a factor of 100 or greater, for example a factor of 500 or greater, including a factor of 1000 or greater, as compared to the initial volume prior to contact with the aqueous medium, in 10 minutes or less, such as 5 minutes or less, including 1 minute or less.

As mentioned above, films of interest are configured to absorb water upon contact with an aqueous medium. While the amount of water that is absorbed by a given film may vary, in some instances the films absorb 10 or more grams of water per gram dry weight of film, such as 25 or more grams of water per gram of dry weight of film, including 50 or more grams of water per gram of dry weight film, upon contact with an aqueous medium.

Highly-swellable polymeric films of interest are those that swell substantially upon contact with a liquid aqueous medium, but do not swell substantially, if at all, upon contact with a gaseous medium that includes water vapor. As such, upon contact with a gaseous medium that includes water vapor (e.g., where the partial pressure of water ranges from 1.0 to 49.8, such as 2.7 to 21.4 mmHg), the films swell little, if at all. As such, any swelling that occurs upon contact with such a gaseous medium as determined by a change in volume is a factor of five or less, such as a factor of 2 or less as compared to the film prior to contact with the gaseous medium.

Highly swellable polymeric films of interest exhibit rapidly swelling behavior without disintegrating upon contact with a liquid aqueous medium. As such, the films swell upon contact with an aqueous medium but do not break up or separate into parts, such that they do not lose intactness or solidness. As such, they do not dissolve upon contact with a liquid aqueous medium. Accordingly, a film that contacts a liquid aqueous medium will remain as a single entity following swelling, and will not go into solution. Therefore, following contact with a liquid aqueous medium, the film can still be manipulated, i.e., handled.

In some instances, the highly-swellable polymeric films are ingestible. As such films are ingestible, they are configured to be ingested or swallowed, i.e., taken into the stomach by drawing through the throat and esophagus with a voluntary muscular action. As such, the films themselves, as well as the components thereof, e.g., polymeric components, binders, plasticizers, porogens (such as described in greater detail below), do not exhibit an unacceptable level of toxicity when employed as intended. In other words, when the films are employed for their intended use, the toxicity level of the films, if present all, is acceptable.

Prior to contact with an aqueous medium, the freestanding films are mechanically stable. Films are flexible, able to easily wrap around rollers and rods and relatively strong under tension, but show little elongation under strain.

Films of interest may include an ionic polymer and may therefore be referred to as polymeric films. The phrase "ionic polymer" refers to a polymer comprising monomeric units having an acidic functional group, such as a carboxyl, sulfate, sulfonate, phosphate or phosphonate group, or a basic functional group, such as an amino, substituted amino or guanidyl group. When in aqueous solution at a suitable pH range, e.g., 7 to 14 pH, an ionic polymer comprising acidic functional groups will be a polyanion, and such a polymer is referred to herein as an "anionic polymer". Likewise, in aqueous solution at a suitable pH range, e.g., 1 to 7 pH, an ionic polymer comprising basic functional groups will be a polycation. Such a polymer is referred to herein as a "cationic polymer". As used herein, the terms ionic polymer, anionic polymer and cationic polymer refer to hydrophilic polymers in which the acidic or basic functional groups are not charged, as well as polymers in which some or all of the acidic or basic functional groups are charged, in combination with a suitable counterion. Suitable anionic polymers include alginates, e.g., alginic acid and salts thereof, polyacrylic acid, dextran sulfate, carboxymethylcellulose, hyaluronic acid, polyglucuronic acid, polymanuronic acid, polygalacturonic acid, polyarabinic acid; chrondroitin sulfate and dextran phosphate. Suitable cationic polymers include chitosan, polyethylenimine, poly-L-lysine, and dimethylaminodextran. Of interest in some instances are polysaccharide anionic polymers. Polysaccharide anionic polymers of interest include alginates, e.g., alginic acid and salts thereof. Alginic acid (i.e., alginate) is a linear copolymer with homopolymeric blocks of (1-4)-linked β-D-mannuronate (M) residues and α-L-guluronate (G) residues. The residues are covalently linked together in different sequences or blocks. The residues can appear in homopolymeric blocks of consecutive G-residues (G-blocks), consecutive M-residues (M-blocks) or alternating M and G-residues (MG-blocks). Also of interest are salts of alginic acid, e.g., sodium alginate, calcium alginate, potassium alginate, etc. The molecular weight of the alginate (e.g., alginic acid or alginate salt thereof) may vary, ranging in some instances from 10,000 to 600,000 Daltons, such as 50,000 to 100,000 Daltons. Alginates of interest will include a percentage of acidic groups sufficient to impart the above described swellability characteristic to the film. As such, where an alginate is employed that does not initially include the desired acidic groups, it may be modified as necessary to provide for the desired acidic groups. For example, where sodium alginate is employed, some of the sodium groups of the sodium alginate may be converted to acidic groups, e.g., by contacting the film with a suitable acid (such as HCl). To impart the desired mechanical properties to the film, the alginates may be cross-linked. For example, where sodium alginate is employed, the alginate may be cross-linked with a divalent cation salt, e.g., calcium chloride, magnesium chloride, etc.

Where desired, the film may include an additional component that provides for acidic, e.g., carboxyl, functional groups. For example, films of interest may include one or more additional polymers that provide for acidic functional groups, e.g., one or more additional anionic polymers that are present in addition to an alginate. Examples of additional anionic polymers of interest that may be present include, but are not limited to both natural and synthetic polymers.

In some instances, the film is a blend of both an alginate and a polyacrylic acid. Polyacrylic acids of interest include both homopolymeric polyacrylic acid as well as copolymers, including both random and block copolymers, of acrylic acid residues and one or more non-acrylic acid residues, e.g., acrylate residues, etc. Where desired, the polyacrylic acid may be cross-linked. When the film includes a blend of alginate to polyacrylic acid polymers, the dry weight ratio of the two types of polymers in the film may vary, and in some instances ranges from 25 to 95%, such as 50 to 80% and including 70 to 80% alginate.

In addition to the polymeric components, the films may further include one or more additional types of components. For example, films may include one or more agents that enhance conductivity of the film upon contact with an aqueous medium. Examples of such components include pore forming agents (i.e., porogens). The term "porogen" as used herein, refers to a chemical compound that is included in the film and, upon contact with an aqueous medium, is removed from the film, e.g., via diffusion, dissolution, and/or degradation, to leave a pore in the resultant film. The diameter of the pores produced by the porogen may vary, ranging in some instances from 1 to 1000 μm, such as 1 to 500 μm and including 1 to 250 μm. Porogens of interest include both inorganic and organic porogens. Inorganic porogens of interest include, but are not limited to: inorganic salts, e.g., NaCl, MgCl2, CaCl2, NH4Cl, NH4PO4, NH4CO3; soluble biocompatible salts; sugars (e.g., sugar alcohols), polysaccharides (e.g., dextran (poly(dextrose)), water soluble small molecules, natural or synthetic polymers, oligomers, or monomers that are water soluble or degrade quickly under physiological conditions, including but not limited to: polyethylene glycol, polyvinyl alcohol, poly(vinylpyrrolidone), pullulan, poly(glycolide), poly(lactide), poly(lactide-co-glycolide), other polyesters, and starches. When present, the total amount of porogen component made up of one or more porogens may vary. In some instances, the amount of porogen component ranges from 1 to 40, including from 5 to 10 dry weight percent of the film.

Where desired, films may include one or more binding agents or binders. Binders of interest include, but are not limited to: celluloses, e.g., methyl cellulose, hydroxymethyl cellulose, hydroxyethyl cellulose, hydroxypropyl cellulose, hydroxypropyl methylcellulose, etc.; polyvinyl pyrrolidone; polyethylene oxides; gums, acrylate polymers; methacrylate polymers; copovidone; etc. When present, the total amount of binder component made up of one or more binding agents may vary. While the total amount of one or more binding agents in the film may vary, in some instances the amount ranges from 1 to 50, such as 5 to 10 dry weight percent of the film.

Where desired, films may include one or more plasticizing agents. Plasticizing agents of interest include, but are not limited to: fatty acids, e.g., oleic acid, palmitic acid, etc.; dioctylphtalate; phospholipid; phosphatidic acid; polyethylene glycol; glycerine; butylhydroxytoluene; salts; saccharides, e.g., sucrose; etc. When present, the total amount of plasticizer component made up of one or more plasticizing agents may vary. In some instances, the amount of plasticizer component ranges from 0.01 to 10, including from 2 to 5 dry weight percent of the film.

FIG. 1 provides an illustration of how a highly-swellable polymeric film swells upon contact with an aqueous medium. On the left side of FIG. 1, dry film 10 has a first volume. Following contact with an aqueous medium as illustrated by the arrow, the swollen film on the right side has a volume that is about 25 times greater than the volume of the dry film.

Ingestible Compositions

Aspects of the invention include ingestible compositions. In these instances, ingestible compositions of interest include both an ingestible component and a highly-swellable film component which is associated therewith. As the compositions are ingestible, they are configured to be ingested or swallowed, i.e., taken into the stomach by drawing through the throat and esophagus with a voluntary muscular action. Accordingly, the compositions are dimensioned so as to be capable of being ingested. In some instances, the compositions have a longest dimension of 30 mm or less, such as 20 mm or less, e.g., 10 mm or less. The volume of the ingestible composition may also vary so long as the composition is suitable for ingestion, where the volume in some instances may be 25 mm$^3$ or less, such as 15 mm$^3$ or less, including 10 mm$^3$ or less.

In the ingestible compositions, the ingestible component is a portion or part of the ingestible composition that is configured for ingestion. The ingestible component may vary widely and may include one or more subcomponents, e.g., a pharmaceutically acceptable solid carrier (which may or may not include an active agent), a device (which may or may not include electronic circuitry), etc. In the ingestible composition, the highly-swellable polymeric film may be associated with an ingestible composition in a number of different ways, e.g., depending on the nature of the ingestible composition, depending on the purpose of the film, etc.

In some instances, the ingestible component includes a pharmaceutically acceptable solid carrier. Pharmaceutically acceptable solid carrier configurations include tablet and capsule configurations. While the pharmaceutically acceptable solid carrier may have a solid configuration, the solid configuration may include a liquid component, such as is found in a liquid capsule, which includes a liquid component present in a solid capsule. In some instances, the pharmaceutically acceptable solid carrier is configured to impart a controlled release profile to an active agent that is associated with the pharmaceutically acceptable solid carrier. Examples of pharmaceutically acceptable solid carriers of interest can be found in Remington's Pharmaceutical Sciences, Mace Publishing Company, Philadelphia, Pa., 17th ed. (1985). In such instances, among other non-mutually exclusive functions, e.g., as described below, the highly-swellable polymeric films may serve to separate the ingestible component from the carrier. For instance, upon contact with an aqueous medium, the resultant swelling of the film may result in the component to which the film is associated being pushed away and separated from the carrier, e.g., tablet or capsule. Such functionality of the film may be desirable, e.g., where association of the carrier material impedes functionality of the ingestible component (such as by blocking access of electrode material to an aqueous environment).

Where desired, the pharmaceutically acceptable solid carrier may include an active agent. Active agents of interest include pharmaceutically active agents as well as non-pharmaceutical active agents, such as diagnostic agents. The phrase "pharmaceutically active agent" (also referred to herein as drugs) refers to a compound or mixture of compounds which produces a physiological result, e.g., a beneficial or useful result, upon contact with a living organism, e.g., a mammal, such as a human. Pharmaceutically active agents are distinguishable from such components as excipients, carriers, diluents, lubricants, binders and other formulating aids, and encapsulating or otherwise protective components. The pharmaceutically active agent may be any molecule, as well as binding portion or fragment thereof, that is capable of modulating a biological process in a living subject. In certain aspects, the pharmaceutically active agent may be a substance used in the diagnosis, treatment, or prevention of a disease or as a component of a medication. The pharmaceutically active agent is capable of interacting with a target in a living subject. The target may be a number of different types of naturally occurring structures, where targets of interest include both intracellular and extracellular targets. Such targets may be proteins, phospholipids, nucleic acids and the like, where proteins are of particular interest. Specific proteinaceous targets of interest include, without limitation, enzymes, e.g., kinases, phosphatases, reductases, cyclooxygenases, proteases and the like, targets comprising domains involved in protein-protein interactions, such as the SH2, SH3, PTB and PDZ domains, structural proteins, e.g., actin, tubulin, etc., membrane receptors, immunoglobulins, e.g., IgE, cell adhesion receptors, such as integrins, etc., ion channels, transmembrane pumps, transcription factors, signaling proteins, and the like. Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; neurological agents, e.g., anti-convulsants, etc. The amount of active agent that is present in the solid carrier may vary. In some instances, the amount of active agent that is present may range from 0.01 to 100% by weight.

Further examples of pharmaceutically acceptable solid carriers and active agents which may or may not be included therein are described in PCT Application Serial No. PCT/US2006/016370 published as WO/2006/116718; PCT Application Serial No. PCT/US2007/082563 published as WO/2008/052136; PCT Application Serial No. PCT/US2007/024225 published as WO/2008/063626; PCT Application Serial No. PCT/US2007/022257 published as WO/2008/066617; PCT Application Serial No. PCT/US2008/052845 published as WO/2008/095183; PCT Application Serial No. PCT/US2008/053999 published as WO/2008/101107; PCT Application Serial No. PCT/

US2008/056296 published as WO/2008/112577; PCT Application Serial No. PCT/US2008/056299 published as WO/2008/112578; PCT Application Serial No. PCT/US2008/077753 published as WO2009/042812; PCT Application Serial No. PCT/US2008/085048 published as WO2009/070773; PCT Application Serial No. PCT/US2009/36231 published as WO2009/111664; PCT Application Serial No. PCT/US2009/049618 published as WO2010/005877; PCT Application Serial No. PCT/US2009/053721 published as WO2010/019778; PCT Application Serial No. PCT/US2009/060713 published as WO2010/045385; PCT Application Serial No. PCT/US2009/064472 published as WO2010/057049; PCT Application Serial No. PCT/US2009/067584 published as WO2010/068818; PCT Application Serial No. PCT/US2009/068128 published as WO2010/075115; PCT Application Serial No. PCT/US2010/020142 published as WO2010/080765; PCT Application Serial No. PCT/US2010/020140 published as WO2010/080764; PCT Application Serial No. PCT/US2010/020269 published as WO2010/080843; PCT Application Serial No. PCT/US2010/028518 published as WO2010/111403; PCT Application Serial No. PCT/US2010/032590 published as WO2010/129288; PCT Application Serial No. PCT/US2010/034186 published as WO2010/132331; PCT Application Serial No. PCT/US2010/055522 published as WO2011/057024; the disclosures of which are herein incorporated by reference.

With such ingestible compositions, the highly-swellable polymeric film may be associated with the ingestible component in a number of different ways. For example, the highly-swellable polymeric film may form a coating or layer that substantially if not completely encloses the ingestible component. Such a configuration may be employed where it is desired to impart shelf-life stability to the ingestible composition. In such instances, the film imparts shelf-life stability to the composition, in that the film enhances the storage stability of the composition by a quantifiable measure as compared to a control or reference composition (i.e., a composition that lacks the shelf-life stability component). Highly-swellable polymeric films of interest may enhance the shelf-life stability of the composition as compared to a suitable control by a magnitude of 2-fold or greater, such as 5-fold or greater including 10-fold or greater, e.g., 25-fold or greater. The presence of the film allows the composition to be stable for extended periods of time during or following manufacture, where the ingestible composition may be stable for one year or longer, such as two years or longer, including five years or longer, following manufacture when the composition is maintained under conditions in which the temperature ranges from 10 to 40° C., the pressure ranges from 0.5 to 2.0 ATM and the relative humidity ranges from 10 to 100%. By "stable" is meant that the functionality of the composition does not degrade to a point that the composition is no longer suitable for use in its intended purpose. For example, if the composition includes an active pharmaceutical agent, the amount of active agent following the storage time period may be 85% or more, such as 90% or more, including 95% or more of the original amount present in the composition following manufacture, e.g., as determined using an HPLC protocol or other suitable analytical technique which can distinguish the amount of active agent from any degradation byproducts, such as oxidation byproducts.

In addition to or instead of a pharmaceutically acceptable solid carrier, ingestible compositions may include a device. The term "device" is used broadly to refer to a mechanical and/or electrical component configured for a particular purpose, where the device may or may not include a circuitry component.

Of interest as devices are ingestible devices, e.g., RFID-enabled devices; ingestible event indicators (also known as ingestible event markers or IEMS), etc. An ingestible event indicator is a device that is dimensioned to be ingestible and includes an identifier circuitry component and, optionally, a current path extender, e.g., a membrane, sometimes referred to herein as a "skirt". Various aspects of an event indicator may include a control device for altering conductance; and a partial power source. The partial power source may include a first material electrically coupled to the control device; and a second material electrically coupled to the control device and electrically isolated from the first material, where the first and second materials are dissimilar.

Upon ingestion, the event indicator contacts a conducting fluid, e.g., stomach fluid. When the event indicator is in contact with the conducting liquid, a current path is formed through the conducting liquid between the first and second materials. The voltage potential created between the materials provides the power for operating the event indicator as well as produces the current flow through the conducting fluid and the system. In one aspect, the event indicator operates in direct current mode. In an alternative aspect, the event indicator controls the direction of the current so that the direction of current is reversed in a cyclic manner, similar to alternating current. The current path through the system is controlled by the control device. Completion of the current path allows for the current to flow and in turn a receiver, not shown, can detect the presence of the current and recognize that the system has been activated and the desired event is occurring or has occurred.

In one aspect, the two materials are similar in function to the two electrodes needed for a direct current power source, such as a battery. The conducting liquid acts as the electrolyte needed to complete the power source. The completed power source is defined by the electrochemical reaction between the dissimilar materials of the event indicator and the completion of the power source is enabled by the fluids of the body. The completed power source may be viewed as a power source that exploits electrochemical conduction in an ionic or a conducting solution such as gastric fluid, blood, or other bodily fluids and some tissues.

In certain aspects, the complete power source or supply is one that is made up of active electrode materials, electrolytes, and inactive materials, such as current collectors and packaging. The active materials are any pair of materials with different electrochemical potentials. Suitable materials are not restricted to metals, and in certain aspects the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable. Where desired, the voltage provided by the two dissimilar electrochemical materials upon contact of the materials of the power source with the target physiological site is 0.001 V or higher, including 0.01 V or higher, such as 0.1 V or higher, e.g., 0.3 V or higher, including 0.5 volts or higher, and including 1.0 volts or higher, where in certain aspects, the voltage ranges from about 0.001 to about 10 volts, such as from about 0.01 to about 10 V.

Anode materials of interest include, but are not limited to: magnesium, zinc, sodium, lithium, iron and alloys thereof, e.g., Al and Zn alloys of Mg, which may or may not be intercalated with a variety of materials such, as graphite with Li, K, Ca, Na, Mg, and the like. Cathode materials of interest include, but are not limited to, copper salts, such as copper salts of iodide, chloride, bromide, sulfate, formate, Fe3+ salts, e.g., orthophosphate, pyrophosphate, silver salts, etc. One or both of the metals may be doped with a non-metal, for example to enhance the voltage output of the battery. Non-metals that may be used as doping agents in certain aspects include, but are not limited to: sulfur, iodine and the like. In certain aspects, the electrode materials are cuprous iodine (CuI) or cuprous chloride (CuCl) as the anode and magnesium (Mg) metal or magnesium alloy as the cathode. Aspects of the present invention use electrode materials that are not harmful to the human body.

In such ingestible compositions, the film may be associated with the event indicator in a number of different ways, where the different ways are not mutually exclusive such that films may be associated with an event indicator in more than one way. For example, a highly-swellable polymer film may cover a portion of at least one of the first or second dissimilar materials. As such, the film may cover a portion or all of the cathode material. Alternatively or in addition, the film may cover a portion or all of the anode material. In such instances, the film may cover 10% or more, 20% or more, 25% or more, 50% or more, including 75% or more, e.g., 90% or more, etc., of the cathode and/or anode materials, including all of the cathode or anode materials.

With respect to current signatures produced by such event indicators, the current signatures may distinguish one class of event indicator from other types or may be universally unique, such as where the current signature is analogous to a human fingerprint which is distinct from any other fingerprint of any other individual and therefore uniquely identifies an individual on a universal level. In various aspects, the control circuit may generate a variety of different types of communications, including but not limited to: RF signals, magnetic signals, conductive (near-field) signals, acoustic signals, etc.

In various aspects, the event indicator may further include a current path extender, such as a membrane, which produces a virtual dipole length between the pair of dissimilar materials (functioning as transmission elements) that is longer than the actual dipole length. In addition to controlling the magnitude of the current path between the materials, such a membrane (sometimes referred to herein as "amplifier" or "skirt") is used to increase the "length" of the current path and, hence, act to boost the conductance path, as disclosed in the PCT application no. PCT/US2008/077753 published as WO2009/042812 and in U.S. Pat. No. 7,978,064, the entire contents of which are incorporated herein by reference. Throughout the disclosure herein, the terms "membrane", "skirt" and "amplifier" are used interchangeably with the term "current path extender" without impacting the scope or the present aspects and the claims herein.

Where desired, an ingestible event indicator may be stably associated in some manner to another ingestible component, e.g., pharmaceutically acceptable carrier component (e.g., as described above). By "stably associated" is meant that the event indicator and second ingestible component, e.g., a pharmaceutically acceptable carrier component, do not separate from each other, at least until administered to the subject in need thereof, e.g., by ingestion. As the event indicators are dimensioned to be ingestible, they are sized so that they can be placed in a mammalian, e.g., human or animal, mouth and swallowed. In some instances, event indicators have a longest dimension that is 30 mm or less, such as 20 mm or less, including 5 mm or less.

Various aspects of ingestible event indicators of interest (including protocols for the fabrication thereof) are described in PCT Application Serial No. PCT/US2006/016370 published as WO/2006/116718; PCT Application Serial No. PCT/US2007/082563 published as WO/2008/052136; PCT Application Serial No. PCT/US2007/024225 published as WO/2008/063626; PCT Application Serial No. PCT/US2007/022257 published as WO/2008/066617; PCT Application Serial No. PCT/US2008/052845 published as WO/2008/095183; PCT Application Serial No. PCT/US2008/053999 published as WO/2008/101107; PCT Application Serial No. PCT/US2008/056296 published as WO/2008/112577; PCT Application Serial No. PCT/US2008/056299 published as WO/2008/112578; PCT Application Serial No. PCT/US2008/077753 published as WO2009/042812; PCT Application Serial No. PCT/US2008/085048 published as WO2009/070773; PCT Application Serial No. PCT/US2009/36231 published as WO2009/111664; PCT Application Serial No. PCT/US2009/049618 published as WO2010/005877; PCT Application Serial No. PCT/US2009/053721 published as WO2010/019778; PCT Application Serial No. PCT/US2009/060713 published as WO2010/045385; PCT Application Serial No. PCT/US2009/064472 published as WO2010/057049; PCT Application Serial No. PCT/US2009/067584 published as WO2010/068818; PCT Application Serial No. PCT/US2009/068128 published as WO2010/075115; PCT Application Serial No. PCT/US2010/020142 published as WO2010/080765; PCT Application Serial No. PCT/US2010/020140 published as WO2010/080764; PCT Application Serial No. PCT/US2010/020269 published as WO2010/080843; PCT Application Serial No. PCT/US2010/028518 published as WO2010/111403; PCT Application Serial No. PCT/US2010/032590 published as WO2010/129288; PCT Application Serial No. PCT/US2010/034186 published as WO2010/132331; PCT Application Serial No. PCT/US2010/055522 published as WO2011/057024; the disclosures of which are herein incorporated by reference.

In certain aspects, the ingestible event indicators are disrupted upon administration to a subject. As such, in certain aspects, the compositions are physically broken, e.g., dissolved, degraded, eroded, etc., following delivery to a body, e.g., via ingestion, injection, etc. The compositions of these aspects are distinguished from devices that are configured to be ingested and survive transit through the gastrointestinal tract substantially, if not completely, intact.

Where desired, an active agent (e.g., as described above) may be present in one or more of the event indicator components, e.g., in the electrochemical materials, the support, the membrane, etc. Examples of such configurations are described in PCT Application Serial No. PCT/US2010/032590 published as WO2010/129288; the disclosures of which are herein incorporated by reference.

In some instances the membrane may be made up partially or completely of a highly-swellable polymeric film. For example, the entire membrane may be fabricated from a highly-swellable polymeric film. Alternatively, a portion of the membrane, such as the outer-periphery of the membrane, may be made up of the highly-swellable polymeric film, with the remainder of the membrane being made up of one or more other suitable materials.

Figure 2:
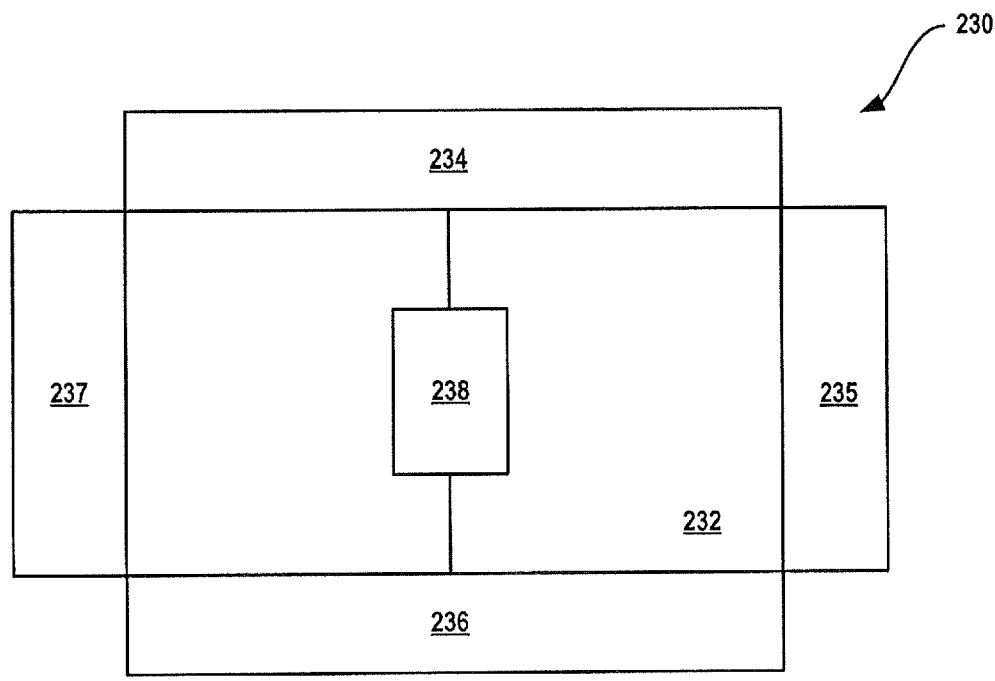
FIG. 2 is a block diagram representation of one aspect of the event indicator system with dissimilar metals positioned on opposite ends of an ingestible event indicator.

With reference to FIG. 2, there is shown one aspect of an ingestible device event indicator system with dissimilar metals positioned on opposite ends as system 230. The system 230 can be used in association with any pharmaceutical product, as mentioned above, and in one aspect, to determine when a patient takes the pharmaceutical product. As indicated above, the scope of the present invention is not limited by the environment and the product that is used with the system 230. For example, the system 230 may be placed within a capsule and the capsule is placed within the conducting liquid. The capsule would then dissolve over a period of time and release the system 230 into the conducting liquid. Thus, in one aspect, the capsule would contain the system 230 and no product. Such a capsule may then be used in any environment where a conducting liquid is present and with any product. For example, the capsule may be dropped into a container filled with jet fuel, salt water, tomato sauce, motor oil, or any similar product. Additionally, the capsule containing the system 230 may be ingested at the same time that any pharmaceutical product is ingested in order to record the occurrence of the event, such as when the product was taken.

In the specific example of the system 230 combined with the pharmaceutical product, as the product or pill is ingested, the system 230 is activated. The system 230 controls conductance to produce a unique current signature that is detected, thereby signifying that the pharmaceutical product has been taken. In other aspects, the current signature may contain information on the ingredients of the ingested pharmaceutical product which may include their chemical composition, date of manufacture, batch number, etc., among other desired information related to the pharmaceutical product which may be a placebo as well. The system 230 includes a framework 232. The framework 232 is a chassis for the system 230 and multiple components are attached to, deposited upon, or secured to the framework 232. In this aspect of the system 230, a digestible material 234 is physically associated with the framework 232. The material 234 may be chemically deposited on, evaporated onto, secured to, or built-up on the framework all of which may be referred to herein as "deposit" with respect to the framework 232. The material 234 is deposited on one side of the framework 232. The materials of interest that can be used as material 234 include, but are not limited to: Cu or CuI, e.g., as described above. The material 234 is deposited by physical vapor deposition, electro-deposition, or plasma deposition, among other protocols. The material 234 may be from about 0.05 to about 500 µm thick, such as from about 5 to about 100 µm thick. The shape is controlled by shadow mask deposition, or photolithography and etching. Additionally, even though only one region is shown for depositing the material, each system 230 may contain two or more electrically unique regions where the material 234 may be deposited, as desired.

At a different side, which may be the opposite side as shown in FIG. 2, another digestible material 236, electrically isolated from the material 234, is deposited, such that materials 234 and 236 are dissimilar. Although not shown, the different side selected may be the side next to the side selected for the material 234. The scope of the present invention is not limited by the side selected and the term "different side" can mean any of the multiple sides that are different from the first selected side. Furthermore, even though the shape of the system is shown as a square, the shape may be any geometrically suitable shape. Materials 234 and 236 are selected such that they produce a voltage potential difference when the system 230 is in contact with conducting liquid, such as body fluids. The materials of interest for material 236 include, but are not limited to: Mg, Zn, or other electronegative metals, e.g., as described above. As indicated above with respect to the material 234, the material 236 may be chemically deposited on, evaporated onto, secured to, or built-up on the framework. Also, an adhesion layer may be employed, as convenient, to help the material 236 (as well as material 234 when needed) to adhere to the framework 232. Adhesion layers of interest for the material 236 are Ti, TiW, Cr or similar material. Anode material and the adhesion layer may be deposited by physical vapor deposition, electro-deposition or plasma deposition. The material 236 may be from about 0.05 to about 500 µm thick, such as from about 5 to about 100 µm thick. However, the scope of the present invention is not limited by the thickness of any of the materials nor by the type of process used to deposit or secure the materials to the framework 232.

Thus, when the system 230 is in contact with the conducting fluid, e.g., a liquid, a current path, an example is shown in FIG. 5, is formed through the conducting liquid between material 234 and 236. A control device 238 is secured to the framework 232 and electrically coupled to the materials 234 and 236. The control device 238 includes electronic circuitry, for example, a memory, a control logic that is capable of controlling and altering the conductance between the materials 234 and 236.

The voltage potential created between the materials 234 and 236 provides the power for operating the system as well as produces the current flow through the conducting fluid and the system. In one aspect, the system operates in direct current mode. In an alternative aspect, the system controls the direction of the current so that the direction of current is reversed in a cyclic manner, similar to alternating current. As the system reaches the conducting fluid or the electrolyte, where the fluid or electrolyte component is provided by a physiological fluid, e.g., stomach acid, the path for current flow between the materials 234 and 236 is completed external to the system 230; the current path through the system 230 is controlled by the control device 238. Completion of the current path allows for the current to flow, through conductive communication through the stomach, and in turn to a receiver, not shown, the receiver capable of detecting presence of the current signature containing information and further recognize that the system 230 has been activated and the desired event is occurring or has occurred.

In one aspect, the two materials 234 and 236 are similar in function to the two electrodes needed for a direct current power source, such as a battery. The conducting liquid acts as the electrolyte needed to complete the power source. The completed power source described is defined by the physical chemical reaction between the materials 234 and 236 of the system 230 and the surrounding fluids of the body. The completed power source may be viewed as a power source that exploits reverse electrolysis in an ionic or a conductive solution such as gastric fluid, blood, or other bodily fluids and some tissues. Additionally, the environment may be something other than a body and the liquid may be any conducting liquid. For example, the conducting fluid may be salt water or a metallic based paint.

Referring again to FIG. 2, the materials 234 and 236 provide the voltage potential to activate the control device 238. Once the control device 238 is activated or powered up, the control device 238 can alter conductance between the materials 234 and 236 in a unique or desired manner. By altering the conductance between materials 234 and 236, the control device 238 is capable of controlling the magnitude of the current through the conducting liquid that surrounds the system 230. This produces a unique current signature that can be detected and measured by a receiver (not shown), which can be positioned internal, over or external to the body.

As described above, in various aspects, the event indicator may further include a current path extender such as a membrane which, for example, produces a virtual dipole length between the pair of transmission elements that is larger than the actual dipole length. As illustrated in FIG. 2, the current path extender or "skirt", shown in portion at 235 and 237, respectively, may be associated with, e.g., secured to, the framework 232. Various shapes and configurations for the skirt are contemplated as within the scope of the present invention. For example, the system 230 may be surrounded entirely or partially by the skirt and the skirt may be positioned along a central axis of the system 230 or off-center relative to a central axis. Thus, the scope of the present invention as claimed herein is not limited by the shape or size of the skirt. Furthermore, in other aspects, the materials 234 and 236 may be separated by one skirt that is positioned in any defined region between the materials 234 and 236.

Figure 3A:
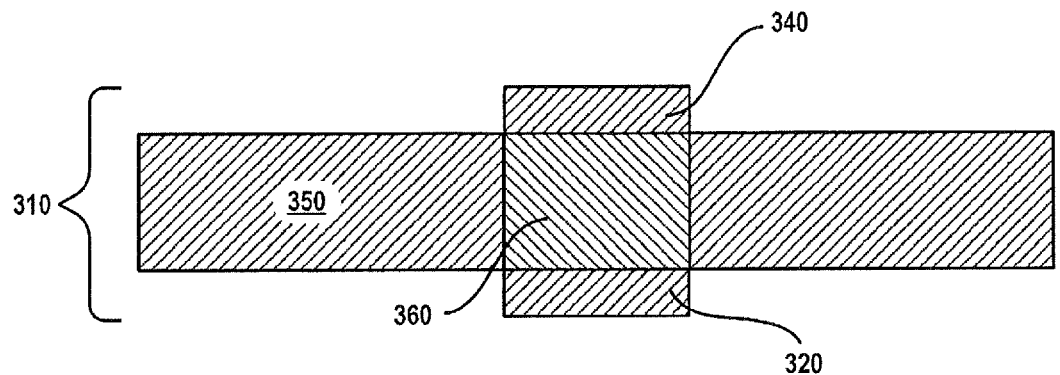
FIGS. 3A and 3B provide side and top views, respectively, of one aspect of an ingestible event indicator.
Figure 3B:
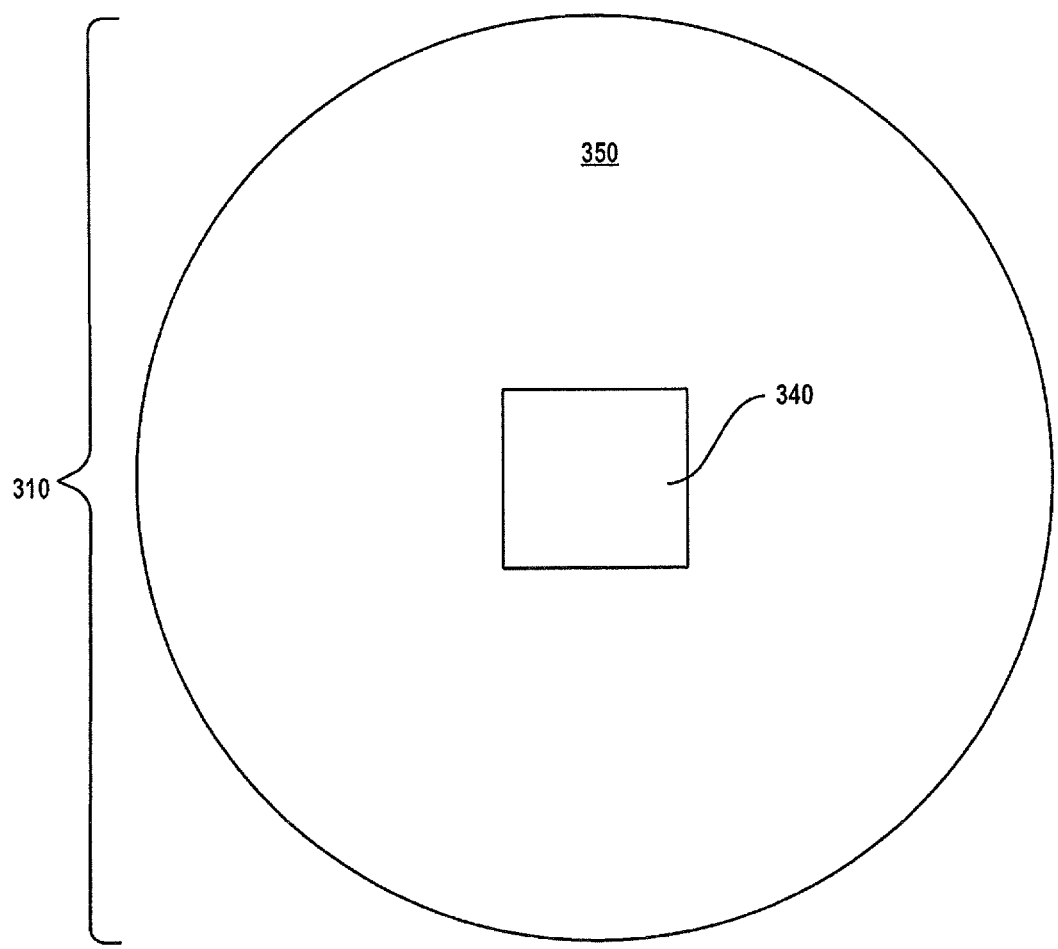

FIG. 3A provides a view of an aspect of an IEM of interest which has a current path extender in the form of a membrane that extends beyond the outer edges of the signal transmission elements to provide a virtual dipole having a length that is longer than the actual dipole between the signal transmission elements. As shown in FIG. 3A, event indicator 310 includes integrated circuit 320, having a first electrochemical material 340 (which may comprise two distinct material layers) and a second electrochemical material 360. Also shown is disc-shaped membrane 350. FIG. 3B provides an overhead view of the event indicator shown in FIG. 3A, showing the disc shape of first electrochemical material 340 and the positioning of the first electrochemical material in the center of disc-shaped membrane 350. The distance that the edge of the membrane may extend beyond the edge of electrodes may vary, and in certain aspects is 0.05 mm or more, e.g., 0.1 mm or more, including 1.0 mm or more, such as 5.0 mm or more and including 10 mm or more, where the distance may not exceed 100 mm in certain aspects.

As can be seen in the aspect depicted in FIGS. 3A & 3B, the first and second electrochemical materials may have any convenient shape, e.g., square, disc, etc. The disc-shaped membrane 350 is a planar disc structure, where the edge of the membrane extends beyond the edge of the first and second electrochemical materials. In the depicted aspect, the radius of the membrane is longer than the radius of the first and second electrochemical materials, e.g., by 1 mm or more, such as by 10 mm or more. Membranes may have "two-dimensional" or "three-dimensional" configurations, as desired. Membrane configurations of interest are further described in PCT Application Serial No. PCT/US2008/077753 published as WO2009/042812, PCT Application Serial No. PCT/US2010/020142 published as WO2010/080765 as well as PCT Application Serial No. PCT/US2010/032590 published as WO2010/129288; the disclosures of which are herein incorporated by reference. The membrane may be fabricated from a number of different materials, where the membrane may be made of a single material or be a composite of two or more different types of materials, as developed in greater detail below. As reviewed above, the membrane may be made up partially or completely of a highly-swellable polymeric film. In such instances, the highly-swellable polymeric film is associated with the support and is configured as a signal amplification that increases a length of a current path between the first and second materials. In certain instances, the membrane will have a mechanical strength sufficient to withstand the mechanical forces typical of the gastrointestinal (GI) tract without folding onto itself and losing its shape. This desired mechanical strength may be chosen to last for at least the duration of the communication, which may be 1 second or longer, such as at least 1 minute or longer, up to 6 hours or longer. In certain aspects, the desired mechanical strength is selected to last least for a period of time ranging from 1 to 30 minutes. The desired mechanical strength can be achieved by proper selection of polymer and/or fillers, or mechanical design (e.g., lamination of multiple layers, or curvature of the amplifier surface) to increase the mechanical strength of the final structure. Membranes of the invention are ones that are electrically insulating. As such, the materials from which the membranes are fabricated are electrically insulating materials. A given material is electrically insulating if it has a resistivity that is two times or greater than the medium in which the device operates, e.g., stomach fluid, such as ten times or greater, including 100 times or greater than the medium in which the device operates.

Figure 4:
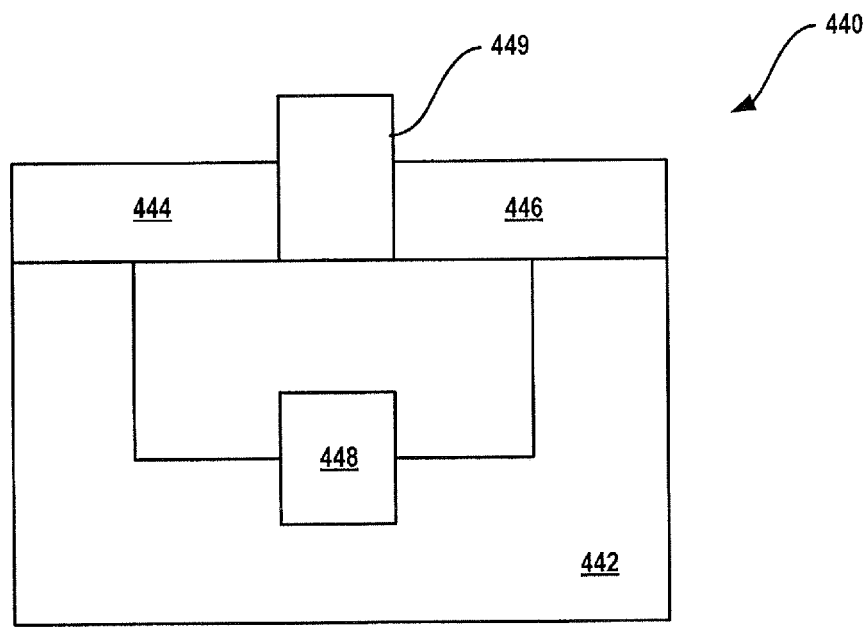
FIG. 4 is a block diagram representation of another aspect of the event indicator system with dissimilar metals positioned on the same end and separated by a non-conducting material.

Referring now to FIG. 4, in another aspect of an ingestible device is shown in more detail as system 440. The system 440 includes a framework 442. The framework 442 is similar to the framework 232 of FIG. 2. In this aspect of the system 440, a digestible or dissolvable material 444 is deposited on a portion of one side of the framework 442. At a different portion of the same side of the framework 442, another digestible material 446 is deposited, such that materials 444 and 446 are dissimilar. More specifically, material 444 and 446 are selected such that they form a voltage potential difference when in contact with a conducting liquid, such as body fluids. Thus, when the system 440 is in contact with and/or partially in contact with the conducting liquid, then a current path, an example is shown in FIG. 5, is formed through the conducting liquid between material 444 and 446. A control device 448 is secured to the framework 442 and electrically coupled to the materials 444 and 446. The control device 448 includes electronic circuitry that is capable of controlling part of the conductance path between the materials 444 and 446. The materials 444 and 446 are separated by a non-conducting skirt 449. Various examples of the skirt 449 are disclosed in PCT Application No. PCT/US2010/032590 published as WO2010/129288; and PCT application Ser. No. PCT/US2008/077753 published as WO2009/042812; the entire disclosure of each is incorporated herein by reference. Once the control device 448 is activated or powered up, the control device 448 can alter conductance between the materials 444 and 446. Thus, the control device 448 is capable of controlling the magnitude of the current through the conducting liquid that surrounds the system 440. As indicated above with respect to system 230, a unique current signature that is associated with the system 440 can be detected by a receiver (not shown) to mark the activation of the system 440. In order to increase the "length" of the current path the size of the skirt 449 is altered. The longer the current path, the easier it may be for the receiver to detect the current.

Referring now to FIG. 5, the system 230 of FIG. 2 is shown in an activated state and in contact with conducting liquid. The system 230 is grounded through ground contact 552. The system 230 also includes a sensor module 274, which is described in greater detail with respect to FIG. 6. Ion or current paths 550 form between material 234 to material 236 through the conducting fluid in contact with the system 230. The voltage potential created between the material 234 and 236 is created through chemical reactions between materials 234/236 and the conducting fluid.

FIG. 5A shows an exploded view of the surface of material 234. The surface of the material 234 is not planar, but rather an irregular surface 554 as shown. The irregular surface 554 increases the surface area of the material and, hence, the area that comes in contact with the conducting fluid.

In one aspect, at the surface of the material 234, there is chemical reaction between the material 234 and the surrounding conducting fluid such that mass is released into the conducting fluid. The term "mass" as used herein refers to protons and neutrons that form a substance. One example includes where the material is CuCl and when in contact with the conducting fluid, CuCl becomes Cu (solid) and Cl⁻ in solution. The flow of ions into the conduction fluid is depicted by the ion paths 550. In a similar manner, there is a chemical reaction between the material 236 and the surrounding conducting fluid and ions are captured by the material 236. The release of ions at the material 234 and capture of ion by the material 236 is collectively referred to as the ionic exchange. The rate of ionic exchange and, hence the ionic emission rate or flow, is controlled by the control device 238. The control device 238 can increase or decrease the rate of ion flow by altering the conductance, which alters the impedance, between the materials 234 and 236. Through controlling the ion exchange, the system 230 can encode information in the ionic exchange process. Thus, the system 230 uses ionic emission to encode information in the ionic exchange.

The control device 238 can vary the duration of a fixed ionic exchange rate or current flow magnitude while keeping the rate or magnitude near constant, similar to when the frequency is modulated and the amplitude is constant. Also, the control device 238 can vary the level of the ionic exchange rate or the magnitude of the current flow while keeping the duration near constant. Thus, using various combinations of changes in duration and altering the rate or magnitude, the control device 238 encodes information in the current flow or the ionic exchange. For example, the control device 238 may use, but is not limited to any of the following techniques namely, Binary Phase-Shift Keying (PSK), Frequency modulation, Amplitude modulation, on-off keying, and PSK with on-off keying.

As indicated above, the various aspects disclosed herein, such as systems 230 and 540 of FIGS. 2 and 4, respectively, include electronic components as part of the control device 238 or the control device 248. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

As indicated above, the system, such as system 230 and 240, control the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the systems 230 and 240 are capable of producing various different unique exchanges or signatures and, thus, provide additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Referring now to FIG. 6, a block diagram representation of the control device 238 is shown. The device 238 includes a control module 662, a counter or clock 664, and a memory 666. Additionally, the device 238 is shown to include a sensor module 672 as well as the sensor module 274, which was referenced in FIG. 5. The control module 662 has an input 668 electrically coupled to the material 234 and an output 670 electrically coupled to the material 236. The control module 662, the clock 664, the memory 666, and the sensor modules 672/274 also have power inputs (some not shown). The power for each of these components is supplied by the voltage potential produced by the chemical reaction between materials 234 and 236 and the conducting fluid, when the system 230 is in contact with the conducting fluid. The control module 662 controls the conductance through logic that alters the overall impedance of the system 230. The control module 662 is electrically coupled to the clock 664. The clock 64 provides a clock cycle to the control module 662. Based upon the programmed characteristics of the control module 662, when a set number of clock cycles have passed, the control module 662 alters the conductance characteristics between materials 234 and 236. This cycle is repeated and thereby the control device 238 produces a unique current signature characteristic. The control module 662 is also electrically coupled to the memory 666. Both the clock 664 and the memory 666 are powered by the voltage potential created between the materials 234 and 236.

The control module 662 is also electrically coupled to and in communication with the sensor modules 672 and 274. In the aspect shown, the sensor module 672 is part of the control device 238 and the sensor module 274 is a separate component. In alternative aspects, either one of the sensor modules 672 and 274 can be used without the other and the scope of the present invention is not limited by the structural or functional location of the sensor modules 672 or 274. Additionally, any component of the system 230 may be functionally or structurally moved, combined, or repositioned without limiting the scope of the present invention as claimed. Thus, it is possible to have one single structure, for example a processor, which is designed to perform the functions of all of the following modules: the control module 662, the clock 664, the memory 666, and the sensor module 672 or 274. On the other hand, it is also within the scope of the present invention to have each of these functional components located in independent structures that are linked electrically and able to communicate.

Referring again to FIG. 6, the sensor modules 672 or 274 can include any of the following sensors: temperature, pressure, pH level, and conductivity. In one aspect, the sensor modules 672 or 274 gather information from the environment and communicate the analog information to the control module 662. The control module then converts the analog information to digital information and the digital information is encoded in the current flow or the rate of the transfer of mass that produces the ionic flow. In another aspect, the sensor modules 672 or 274 gather information from the environment and convert the analog information to digital information and then communicate the digital information to control module 662. In the aspect shown in FIG. 5, the sensor module 274 is shown as being electrically coupled to the materials 234 and 236 as well as the control device 238. In another aspect, as shown in FIG. 6, the sensor module 274 is electrically coupled to the control device 238 at connection 678. The connection 678 acts as both a source for power supply to the sensor module 274 and as a communication channel between the sensor module 274 and the control device 38.

Figure 5B:
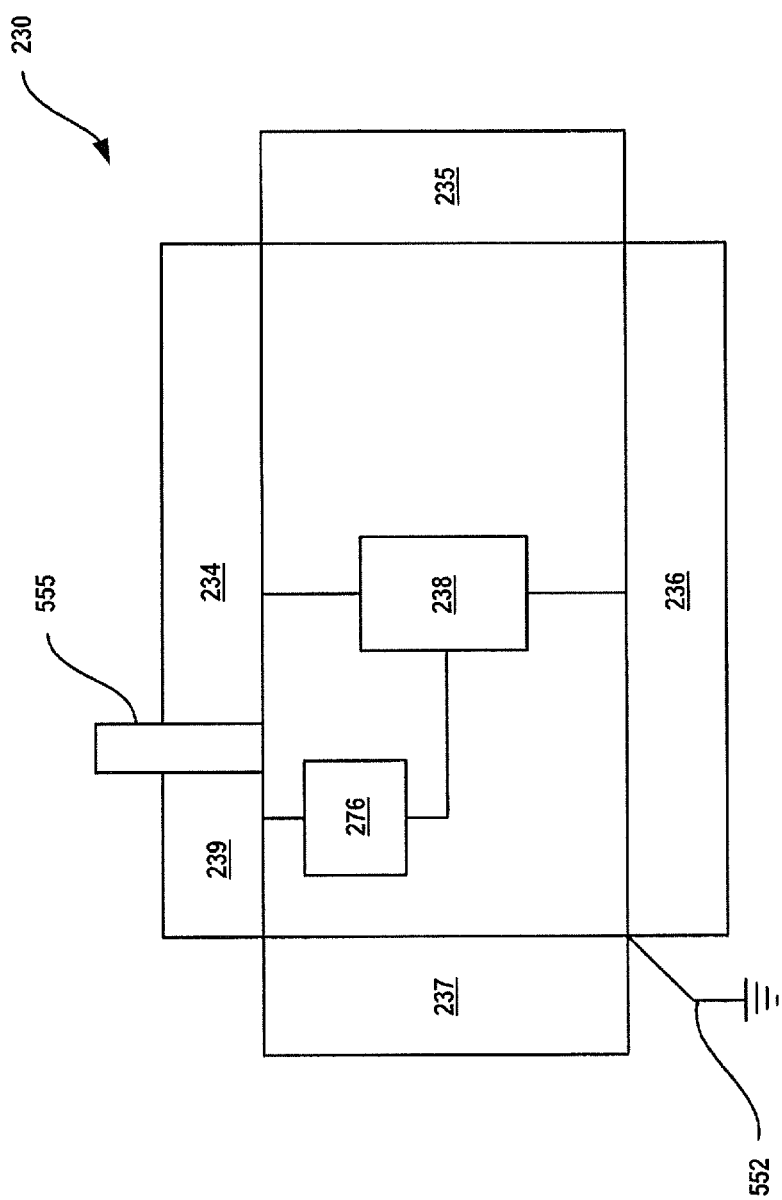
FIG. 5B shows the event indicator system of FIG. 5 with a pH sensor unit.

Referring now to FIG. 5B, the system 230 includes a pH sensor module 276 connected to a material 239, which is selected in accordance with the specific type of sensing function being performed. The pH sensor module 276 is also connected to the control device 238. The material 239 is electrically isolated from the material 234 by a non-conductive barrier 555. In one aspect, the material 239 is platinum. In operation, the pH sensor module 276 uses the voltage potential difference between the materials 234/236. The pH sensor module 276 measures the voltage potential difference between the material 234 and the material 239 and records that value for later comparison. The pH sensor module 276 also measures the voltage potential difference between the material 239 and the material 236 and records that value for later comparison. The pH sensor module 276 calculates the pH level of the surrounding environment using the voltage potential values. The pH sensor module 276 provides that information to the control device 238. The control device 238 varies the rate of the transfer of mass that produces the ionic transfer and the current flow to encode the information relevant to the pH level in the ionic transfer, which can be detected by a receiver (not shown). Thus, the system 230 can determine and provide the information related to the pH level to a source external to the environment.

As indicated above, the control device 238 can be programmed in advance to output a pre-defined current signature. In another aspect, the system can include a receiver system that can receive programming information when the system is activated. In another aspect, not shown, the switch 664 and the memory 666 can be combined into one device.

In addition to the above components, the system 230 may also include one or other electronic components. Electrical components of interest include, but are not limited to: additional logic and/or memory elements, e.g., in the form of an integrated circuit; a power regulation device, e.g., battery, fuel cell or capacitor; a sensor, a stimulator, etc.; a signal transmission element, e.g., in the form of an antenna, electrode, coil, etc.; a passive element, e.g., an inductor, resistor, etc.

As mentioned above, highly-swellable polymeric films may be associated with the ingestible event marker in a number of different, non-mutually exclusive ways. For example, the film may cover a portion of at least one of the first or second dissimilar materials. As such, the film may cover a portion or all of the cathode material. Alternatively or in addition, the film may cover a portion or all of the anode material. In such instances, the film may cover 10% or more, 20% or more, 25% percent or more, 50% or more, including 75% percent or more, e.g., 90% or more, of the cathode and/or anode material, including all of the cathode material or anode material.

Figure 7:
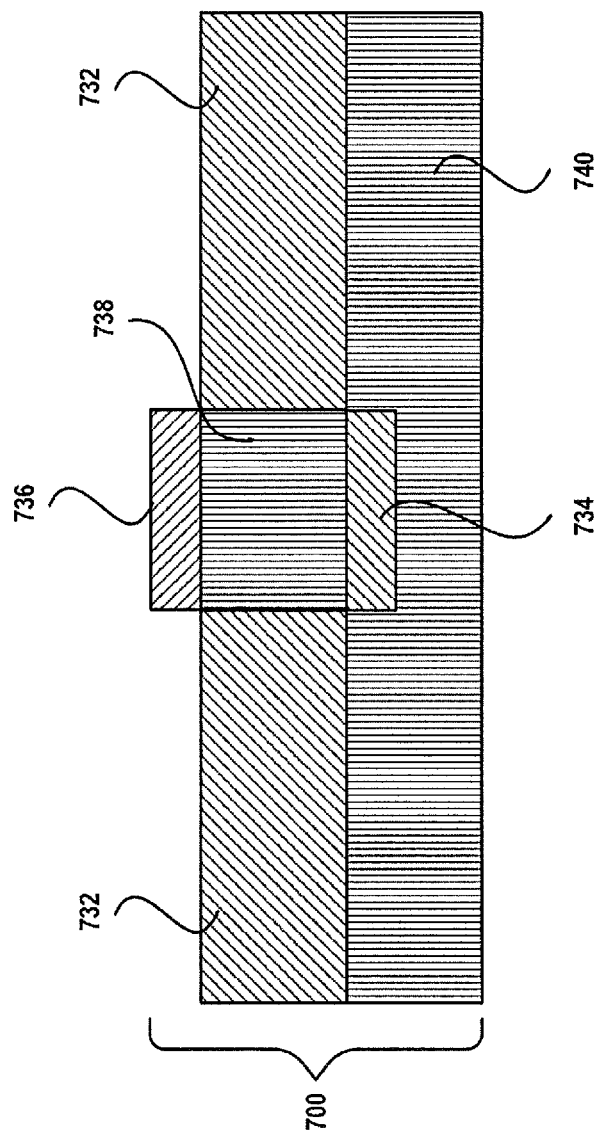
FIG. 7 shows an event indicator having a highly-swellable polymeric film covering the entire surface of the anode.

FIG. 7 provides an illustration of an ingestible event indicator 700 that includes a highly-swellable polymeric film covering all of the anode material. Similar to the event indicator shown in FIG. 2, event indicator 700 includes framework 732 and control device 738, with cathode material 736 on one surface thereof and anode material 734 on the opposite surface thereof. Covering all of the surface of anode material 734 and corresponding surface of framework 732 is highly-swellable polymeric film 740.

Highly-swellable polymeric films such as 740 illustrated in FIG. 7 may serve one or more non-mutually exclusive functions when associated with the ingestible event marker. For example, the highly-swellable polymeric film may serve to inhibit reaction of at least one of the first material or second material with ambient moisture. The term "inhibit" is employed to refer to both substantially impeding any reaction as well as completely stopping any reaction, at least for a given period of time, such as a storage period of time, which may be one week or longer, one month or longer, six months or longer, one year or longer, etc. As such, any reaction that does occur between the first and/or second material and moisture in the ambient environment of the composition is 5.0% or less, including 2.5% or less, such as 1.0% or less, as compared to the reaction which occurs with a control composition lacking the film. In some instances, the film functions to improve shelf-life stability of the composition, e.g., as described above, and therefore enhances the storage stability of the composition by a quantifiable measure as compared to a control composition that lacks the shelf-life stability component. The film may enhance the shelf-life stability of the composition as compared to a suitable control by a magnitude of 2-fold or greater, such as 5-fold or greater including 10-fold or greater, e.g., 25-fold or greater. The presence of the film component allows the composition to be stable for extended periods of time during or following manufacture, where the ingestible composition may be stable for one year or longer, such as two years or longer, including five years or longer, following manufacture when the composition maintained under conditions in which the temperature ranges from 10 to 40° C., the pressure ranges from 0.5 to 2.0 ATM and the relative humidity ranges from 10 to 100%. By "stable" is meant that the functionality of the composition does not degrade to a point that the composition is no longer suitable for use in its intended purpose. For example, if the composition includes a circuitry component, e.g., an ingestible event marker (such as described in greater detail below) or a micro-battery, the circuitry component continues to function for its intended purpose for the period of time between manufacture and ingestion when stored under the conditions described above. If the composition includes an active pharmaceutical agent, the amount of active agent following the storage time period may be 85% or more, such as 90% or more, including 95% or more of the original amount present in the composition following manufacture, e.g., as determined using an HPLC protocol or other suitable analytical technique which can distinguish the amount of active agent from any degradation byproducts, such as oxidation byproducts.

Another function that the film may serve is to provide for conduction between at least one of the first and second materials and an aqueous medium when the ingestible composition is placed in the aqueous medium. As the films are conductive upon swelling, when compositions containing such films are placed into an aqueous medium and the film swells, the films provide for conduction between the first and/or second materials and the aqueous medium. As such, the films can serve to improve the functionality of the ingestible indicator, by providing for conductive communication between the marker and the aqueous environment into which it is placed during use. In some instances, the films provide for a region of conductivity which is known to provide for a signal that is sufficient for the intended purpose of the event marker. In other words, the films may provide a region of consistent conductivity that is known to provide for adequate functionality of the event marker, despite variations in the local environment. For example, the presence of food particles in the local environment, proximity to the gastric mucosa, or variations in the pH and composition of stomach contents may alter the local aqueous environment in which the event marker may be present. The conductivity of the film in the swollen state may be selected to provide for a consistent local environment over a broad range of differing stomach conditions In some instances, improvement of functionality results because the presence of the swollen conductive film impedes the blockage of the first and/or second materials by non-conductive entities that may be present in the environment of the ingestible event marker. Examples of such non-conductive potentially interfering entities that may be present in the environment of the ingestible composition include, but are not limited to: food particles, tissue such as gastrointestinal lining, non-conductive components of the ingestible event marker, and the like. By forming a conductive film over the first and second materials upon swelling, the film serves to prevent contact of non-conductive entities to the materials and thereby improves the function of the composition.

In some instances, event indicators include a highly-swellable film associated with the first and/or second materials and a distinct protective barrier made up of different components and in turn associated with the film, such that the film is between the protective barrier and the first and/or second dissimilar material. Protective barriers which may be employed in such compositions may vary. Examples of such barriers include, but are not limited to, layers that may include one or more of: lipids and functionally analogous materials; pharmaceutically acceptable polymeric materials, etc., e.g., as described in pending U.S. application Ser. No. 13/304,260, the disclosure of which application is herein incorporated by reference.

Figure 8:
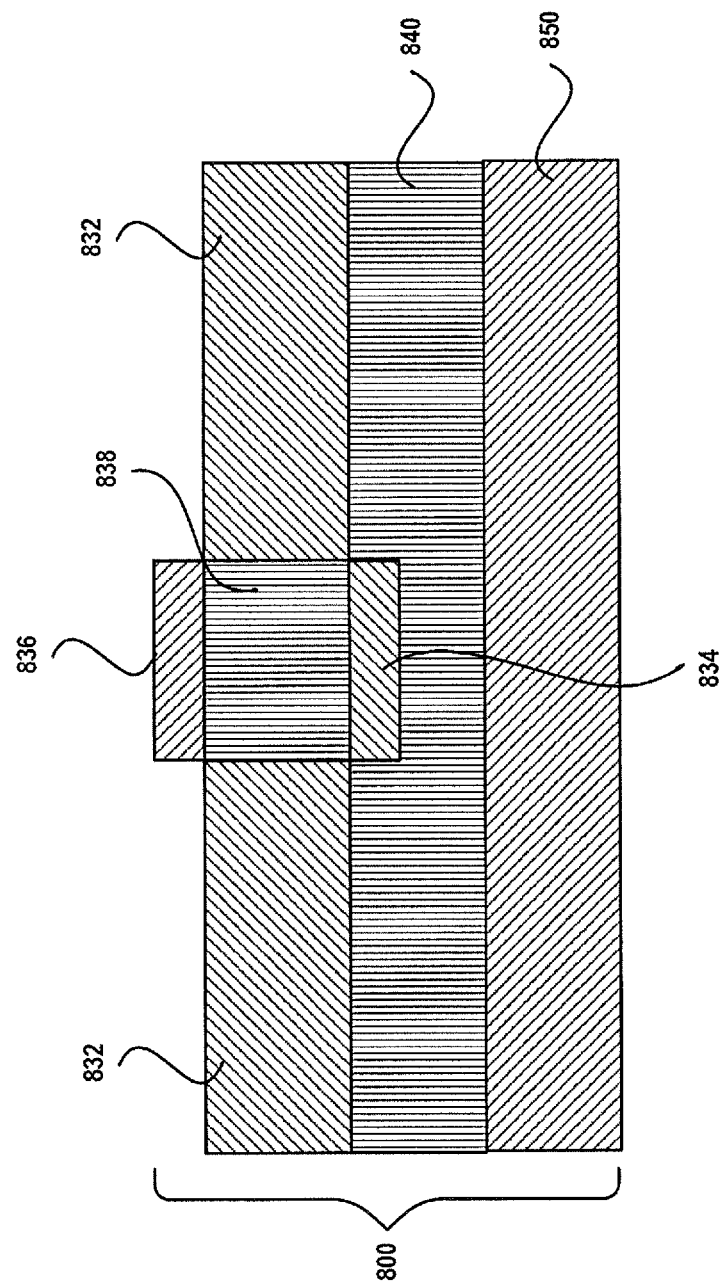
FIG. 8 shows an event indicator having a highly-swellable polymeric film covering the entire surface of the anode, wherein the highly-swellable polymeric film is further covered by a protective barrier.

An example of such a composition is depicted in FIG. 8. In FIG. 8, event indicator 800 is analogous to event indicator 700 shown in FIG. 7. As such, event indicator 800 includes framework 832 and control device 838. On a first surface of control device 838 is cathode material 836 and on a second surface of control device 838 opposite the cathode material 836 is anode material 834. Covering all of cathode material 834 and the corresponding surface of framework 832 is highly-swellable polymeric film 840. On the surface of highly-swellable polymeric film 840 is protective barrier 850, such as a lipid protective barrier, e.g., as described in U.S. application Ser. No. 13/304,260, the disclosure of which application is herein incorporated by reference.

Figure 9A:
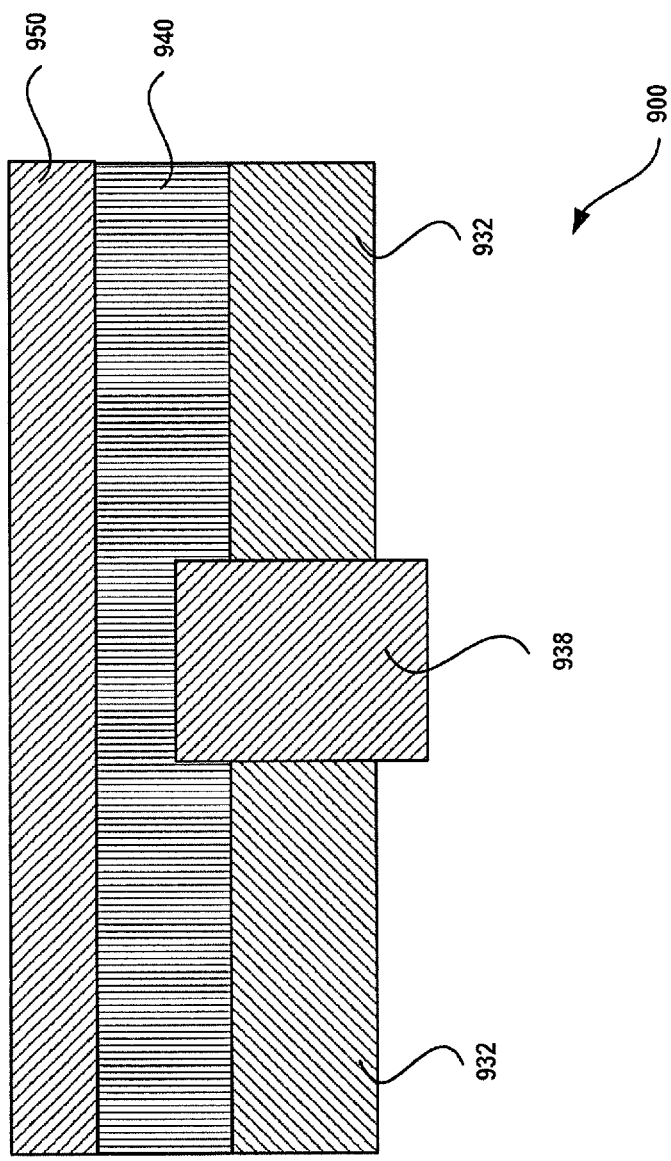
FIG. 9A shows an event indicator in which the anode is covered by a highly-swellable polymeric film and a protective barrier.
Figure 9B:
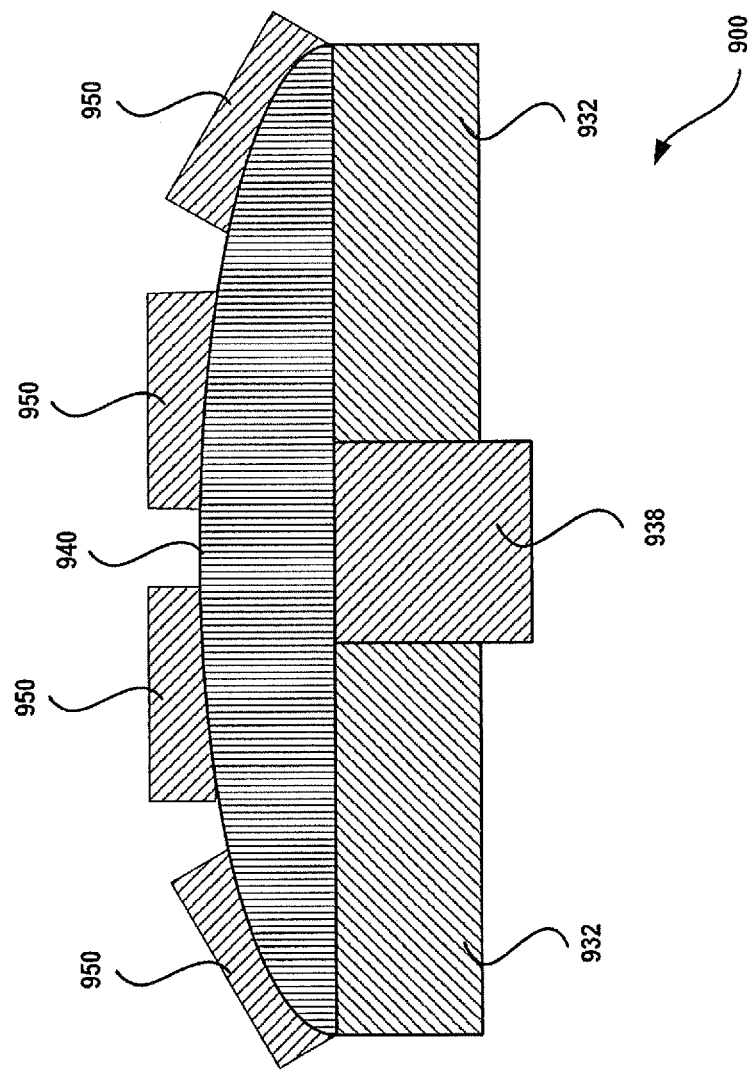
FIG. 9B shows the same event indicator following contact with an aqueous medium, where the film has swollen in a manner that physically disrupts the protective barrier.

In an event indicator as illustrated in FIG. 8, at least one of the purposes of the highly-swellable polymeric film is to disrupt the protective barrier upon contact with a liquid aqueous medium and thereby ensure proper functioning of the event indicator. As illustrated in FIG. 9A, prior to contact with an aqueous medium, event indicator 900 includes control device 938 in framework 932. Covering control device 938 on the anode side is highly-swellable polymeric film 940. Covering the surface of highly-swellable polymeric film 940 which is opposite control device 938 is protective barrier 950. Upon contact with an aqueous medium, highly swellable polymeric film 940 swells as shown in FIG. 9B. Upon swelling, film 940 breaks apart protective barrier 950, ensuring access of the aqueous medium to the conductive highly-swellable polymeric film 940 and thereby proper functioning of the device.

Other Minimally Dimensioned Components

Aspects of the invention further include compositions that are not necessarily ingestible. Such compositions may include a highly-swellable polymeric film (e.g., as described in greater detail above) physically associated with a minimally dimensioned component. While the minimally dimensioned component may vary, e.g., as described above, in some instances the minimally dimensioned component is a micro-battery. Micro-batteries of interest may include "all-solid" batteries, and may include components of a battery, such as current collectors, positive and negative electrodes, an electrolyte, in a minimally dimensioned structure, e.g., as described above. In some instances, micro-batteries of interest are thin films, which may be obtained by deposition, such as by physical vapor deposition (PVD) or chemical vapor deposition (CVD). The micro-battery may take a variety of different configurations, such as but not limited to: a chip configuration, a cylinder configuration, a spherical configuration, a disc configuration, etc., where a particular configuration may be selected based on intended application, method of manufacture, etc. In some instances, the micro-battery is dimensioned to have a width ranging from about 0.05 mm to about 1 mm, such as from about 0.1 mm to about 0.2 mm; a length ranging from about 0.05 mm to about 1 mm, such as from about 0.1 mm to about 0.2 mm and a height ranging from about 0.1 mm to about 1 mm, such as from about 0.05 mm to about 0.3 mm, including from about 0.1 mm to about 0.2 mm. In certain instances, the micro-battery is 1 $mm^3$ or smaller, such as 0.1 $mm^3$ or smaller, including 0.2 $mm^3$ or smaller. In such instances the film may serve to enhance stability of the component, e.g., by improving shelf-life, etc., such as described above.

Systems

Also provided are systems that include an ingestible device, e.g., an event indicator, and a detection component, e.g., in the form of a receiver. Receivers of interest are those configured to detect, e.g., receive, a communication from an ingestible device, e.g., RFID ingestible device, event indicator, etc. The signal detection component may vary significantly depending on the nature of the communication that is generated by the ingestible device. As such, the receiver may be configured to receive a variety of different types of signals, including but not limited to: RF signals, magnetic signals, conductive (near field) signals, acoustic signals, etc. In certain aspects, the receiver is configured to receive a signal conductively from an event indicator, such that the two components use the body of the patient as a communication medium. As such, communication that is transferred between event indicator and the receiver travels through the body, and requires the body as the conduction medium. The event indicator communication may be transmitted through and received from the skin and other body tissues of the subject body in the form of electrical alternating current (a.c.) voltage signals that are conducted through the body tissues. This communication protocol has the advantage that the receivers may be adaptably arranged at any desired location on the body of the subject, whereby the receivers are automatically connected to the required electrical conductor for achieving the signal transmission, i.e., the signal transmission is carried out through the electrical conductor provided by the skin and other body tissues of the subject.

The receivers of interest include external, semi-implantable, and implantable receivers. In external aspects, the receiver is ex vivo, by which is meant that the receiver is present outside of the body during use. Examples include wearable patches, e.g., adhesive patches, torso bands, wrist(s) or arm bands, jewelry, apparel, mobile devices such as phones, attachments to mobile devices, etc. Where the receiver is implanted, the receiver is in vivo. Examples include cardiac can and leads, under-the-skin implants, etc. Semi-implantable devices include those designed to be partially implanted under the skin.

In certain aspects, the receiver may be configured to provide data associated with a received signal to a location external to said subject. For example, the receiver may be configured to provide data to an external data receiver, e.g., which may be in the form of a monitor (such as a bedside monitor), a computer, a personal digital assistant (PDA), phone, messaging device, smart phone, etc. The receiver may be configured to retransmit data of a received communication to the location external to said subject. Alternatively, the receiver may be configured to be interrogated by an external interrogation device to provide data of a received signal to an external location.

Receivers may be configured variously, e.g., with various signal receiving elements, such as electrodes, various integrated circuit components, one or more power components (such as power receivers or batteries), signal transmission components, housing components, etc.

In one aspect, for example, the receiver includes one or more of: a high power-low power module; an intermediary module; a power supply module configured to activate and deactivate one or more power supplies to a high power processing block; a serial peripheral interface bus connecting master and slave blocks; and a multi-purpose connector, as further described in PCT Application Serial No. PCT/US2009/068128 published as WO2010/075115, infra.

Receivers of interest include, but are not limited to, those receivers disclosed in: PCT Application Serial No. PCT/US2006/016370 published as WO 2006/116718; PCT Application Serial No. PCT/US2008/52845 published as WO 2008/095183; PCT Application Serial No. PCT/US2007/024225 published as WO 2008/063626; PCT Application Serial No. PCT/US2008/085048 published as WO 009/070773; PCT Application Serial No. PCT/US2009/068128 published as WO2010/075115; and PCT Application Serial No. US2012/047076 filed on Jul. 21, 2012; the disclosures of which applications (and particularly receiver components thereof) are herein incorporated by reference.

In certain instances, the signal receiver includes a set of two or more, such as two or three, electrodes that provide for dual functions of signal receiving and sensing. For example, in addition to receiving signal, the electrodes can also serve additional sensing functions. Where desired, the electrodes may be used to generate electrocardiogram data. From that data, there are many kinds of processing that can be done, e.g., to detect various cardiac events, such as tachycardia, fibrillations, heart rate, etc. The obtained electrocardiogram data can be used to titrate medications, or be used for alerts when an important change or significant abnormality in the heart rate or rhythm is detected. This data may also be helpful in monitoring heart rate in patients who do not have pacemakers or as an alternative to patients who might normally require a Holter monitor or a Cardiac Event Monitor, portable devices for continuously monitoring the electrical activity of the heart for twenty-four hours or other devices. An extended recording period is useful for observing occasional cardiac arrythmias that are difficult to identify in shorter time periods.

Figure 10:
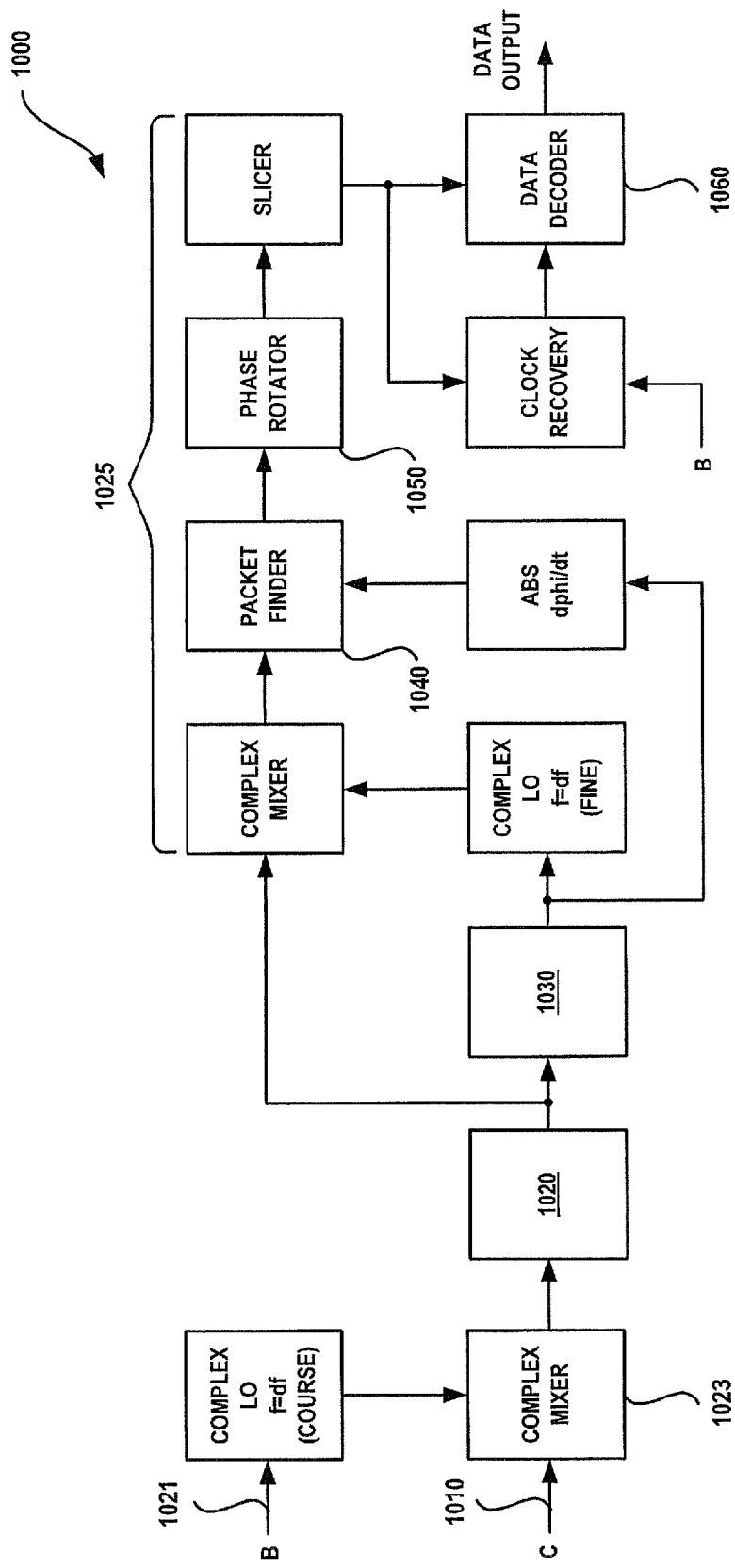
FIG. 10 is a functional block diagram of a demodulation circuit that performs coherent demodulation that may be present in a receiver, according to one aspect.

In some instances, two or more different demodulation protocols may be employed to decode a given received signal. In some instances, both a coherent demodulation protocol and a differential coherent demodulation protocol may be employed. FIG. 10 provides a functional block diagram of how a receiver may implement a coherent demodulation protocol, according to one aspect of the invention. It should be noted that only a portion of the receiver is shown in FIG. 10. FIG. 10 illustrates the process of mixing the signal down to baseband once the carrier frequency (and carrier signal mixed down to carrier offset) is determined. A carrier signal 1021 is mixed with a second carrier signal 1022 at mixer 1023. A narrow low-pass filter 1020 is applied of appropriate bandwidth to reduce the effect of out-of-bound noise. Demodulation occurs at functional blocks 1025 in accordance with the coherent demodulation scheme of the present invention. The unwrapped phase 1030 of the complex signal is determined. An optional third mixer stage, in which the phase evolution is used to estimate the frequency differential between the calculated and real carrier frequency can be applied. The structure of the packet is then leveraged to determine the beginning of the coding region of the BPSK signal at block 1040. Mainly, the presence of the sync header, which appears as an FM porch in the amplitude signal of the complex demodulated signal is used to determine the starting bounds of the packet. Once the starting point of the packet is determined the signal is rotated at block 1050 on the IQ plane and standard bit identification and eventually decoded at block 1060.

In addition to demodulation, the trans-body communication module may include a forward error correction module, which module provides additional gain to combat interference from other unwanted signals and noise. Forward error correction functional modules of interest include those described in PCT Application Serial No. PCT/US2007/024225 published as WO 2008/063626; the disclosure of which application is herein incorporated by reference. In some instances, the forward error correction module may employ any convenient protocol, such as Reed-Solomon, Golay, Hamming, BCH, and Turbo protocols to identify and correct (within bounds) decoding errors.

Receivers of the invention may further employ a beacon functionality module. In various aspects, a beacon switching module may employ one or more of the following: a beacon wakeup module, a beacon signal module, a wave/frequency module, a multiple frequency module, and a modulated signal module.

Figure 11:
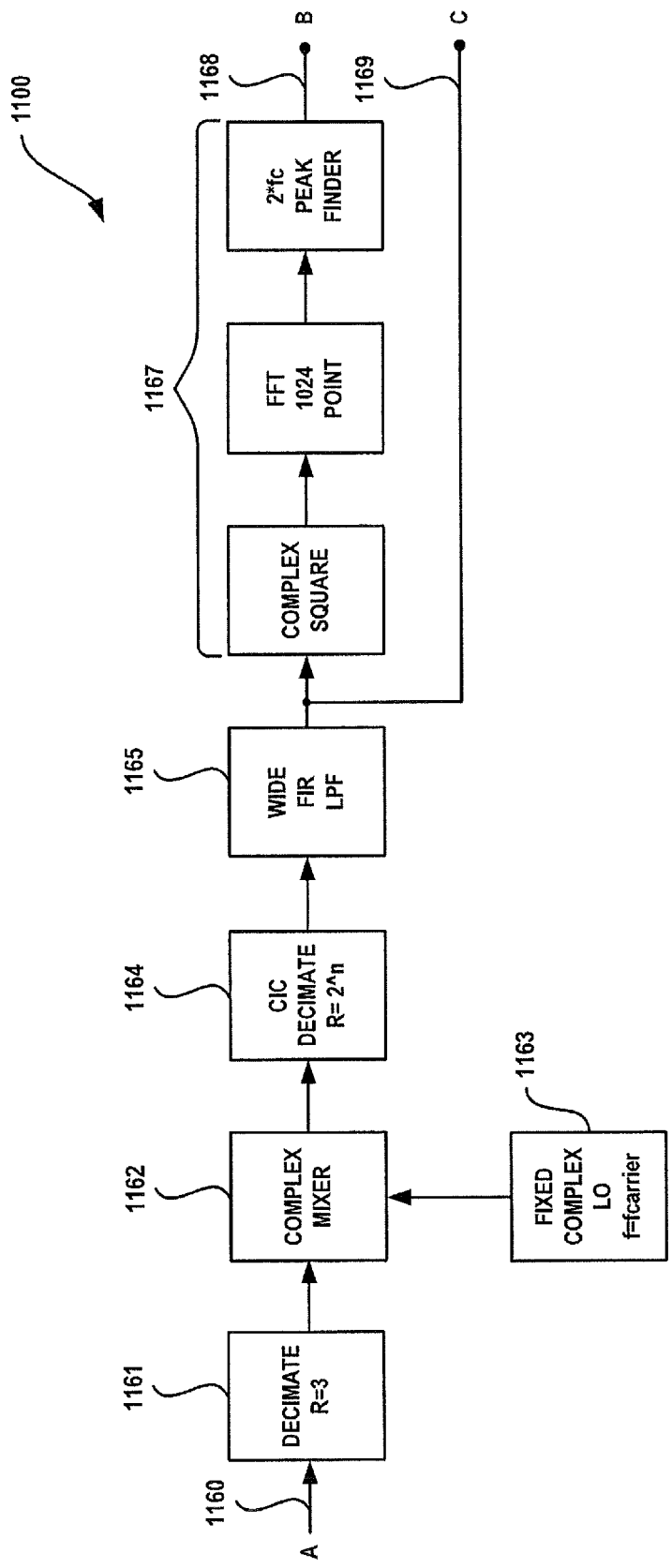
FIG. 11 illustrates a functional block diagram for a beacon module within a receiver, according to one aspect.

A view of a beacon module is provided in the functional block diagram shown in 11. The scheme outlined in FIG. 11 outlines one technique for identifying a valid beacon. The incoming signal 1160 represents the signals received by electrodes, bandpass filtered (such as from 10 KHz to 34 KHz) by a high frequency signaling chain (which encompasses the carrier frequency), and converted from analog to digital. The signal 1160 is then decimated at block 1161 and mixed at the nominal drive frequency (such as, 12.5 KHz, 20 KHz, etc.) at mixer 1162. The resulting signal is decimated at block 1164 and low-pass filtered (such as 5 KHz BW) at block 1165 to produce the carrier signal mixed down to carrier offset-signal 1169. Signal 1169 is further processed by blocks 1167 (fast Fourier transform and then detection of two strongest peaks) to provide the true carrier frequency signal 1168. This protocol allows for accurate determination of the carrier frequency of the transmitted beacon. Further examples of beacon functionality modules are described in PCT Application Serial No. PCT/US2008/085048 published as WO 2009/070773; the disclosure of which application is herein incorporated by reference.

Figure 12:
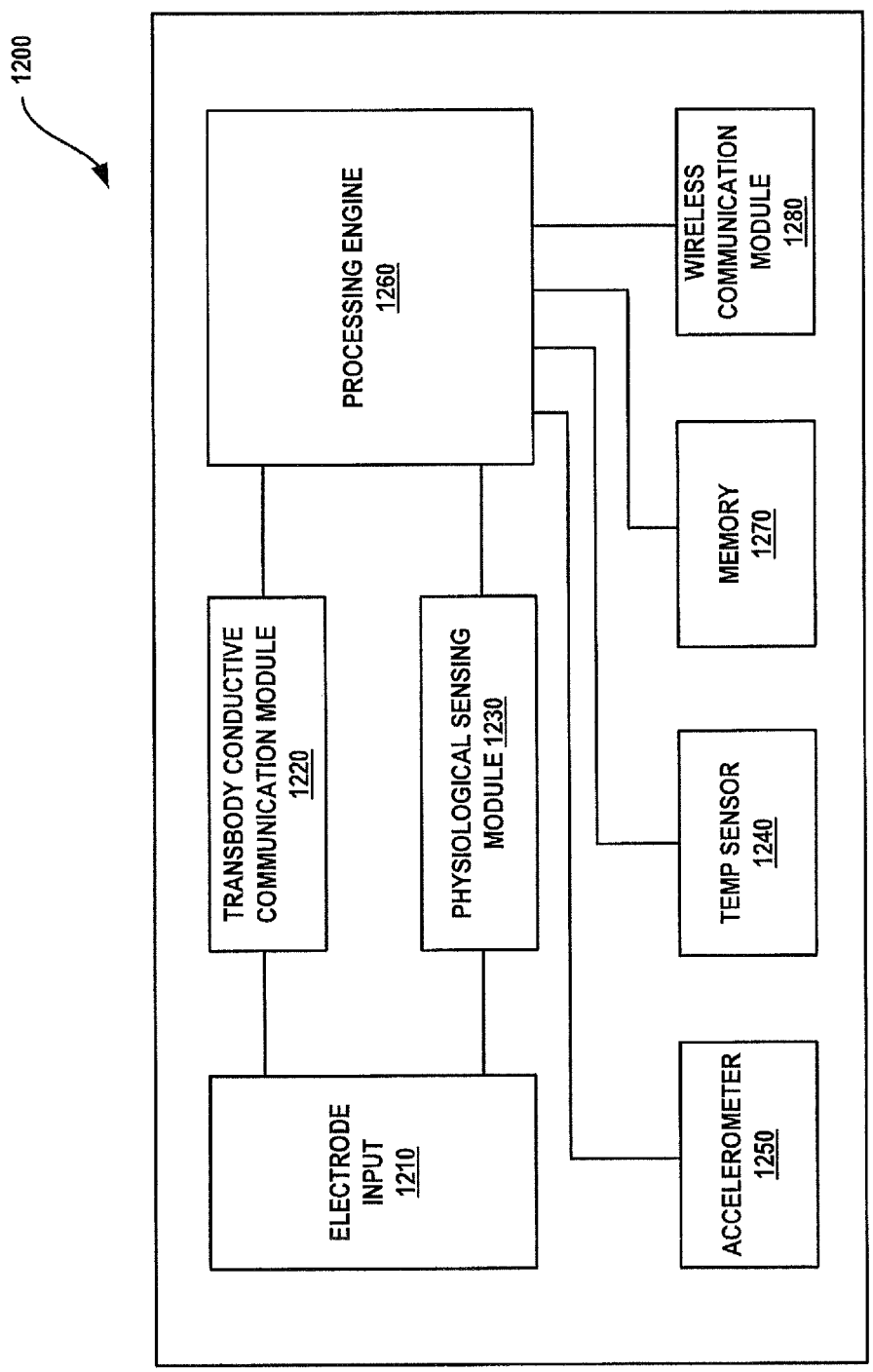
FIG. 12 is a block diagram of different functional modules that may be present in a receiver, according to one aspect.

FIG. 12 provides a block functional diagram of an integrated circuit component of a signal receiver according to an aspect of the invention. In FIG. 12, receiver 1200 includes electrode input 1210. Electrically coupled to the electrode input 1210 are trans-body conductive communication module 1220 and physiological sensing module 1230. In one aspect, trans-body conductive communication module 1220 is implemented as a high frequency (HF) signal chain and physiological sensing module 1230 is implemented as a low frequency (LF) signal chain. Also shown are CMOS temperature sensing module 1240 (for detecting ambient temperature) and a three-axis accelerometer 1250. Receiver 1200 also includes a processing engine 1260 (for example, a microcontroller and digital signal processor), non-volatile memory 1270 (for data storage) and wireless communication module 1280 (for data transmission to another device, for example in a data upload action).

Figure 13:
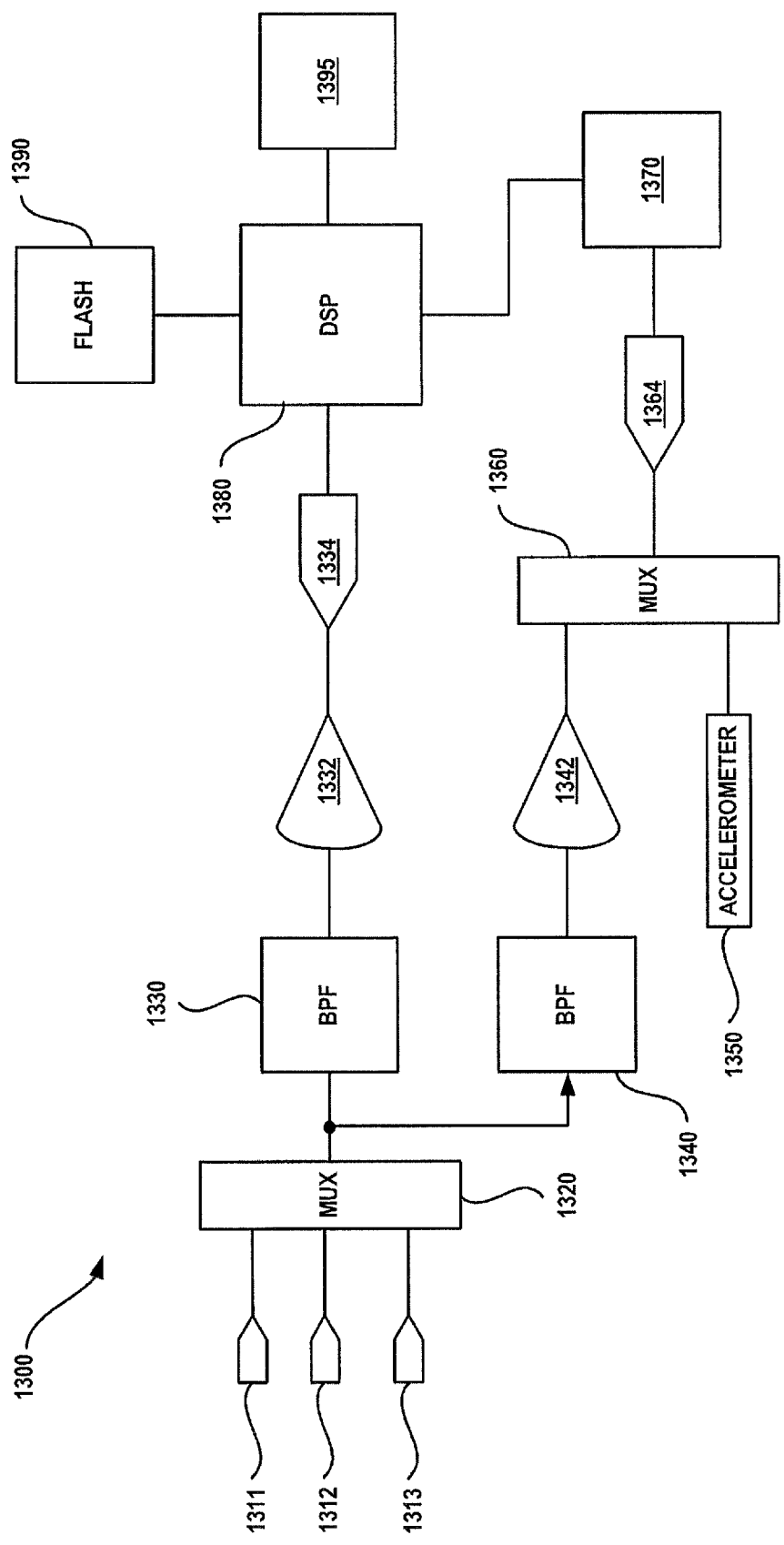
FIG. 13 is a block diagram of a receiver, according to one aspect.

FIG. 13 provides a more detailed block diagram of a circuit configured to implement the block functional diagram of the receiver depicted in FIG. 12, according to one aspect of the invention. In FIG. 13, receiver 1300 includes electrodes e1, e2 and e3 (1311, 1312 and 1313) which, for example, receive the conductively transmitted signals by an IEM and/or sense physiological parameters or biomarkers of interest. The signals received by the electrodes 1311, 1312, and 1313 are multiplexed by multiplexer 1320 which is electrically coupled to the electrodes.

Multiplexer 1320 is electrically coupled to both high band pass filter 1330 and low band pass filter 1340. The high and low frequency signal chains provide for programmable gain to cover the desired level or range. In this specific aspect, high band pass filter 1330 passes frequencies in the 10 KHz to 34 KHz band while filtering out noise from out-of-band frequencies. This high frequency band may vary, and may include, for example, a range of 3 KHz to 300 KHz. The passing frequencies are then amplified by amplifier 1332 before being converted into a digital signal by converter 834 for input into high power processor 1380 (shown as a DSP) which is electrically coupled to the high frequency signal chain.

Low band pass filter 1340 is shown passing lower frequencies in the range of 0.5 Hz to 150 Hz while filtering out out-of-band frequencies. The frequency band may vary, and may include, for example, frequencies less than 300 Hz, such as less than 200 Hz, including less than 150 Hz. The passing frequency signals are amplified by amplifier 1342. Also shown is accelerometer 1350 electrically coupled to second multiplexer 1360. Multiplexer 1360 multiplexes the signals from the accelerometer with the amplified signals from amplifier 1342. The multiplexed signals are then converted to digital signals by converter 1364 which is also electrically coupled to low power processor 1370.

In one aspect, a digital accelerometer (such as one manufactured by Analog Devices), may be implemented in place of accelerometer 1350. Various advantages may be achieved by using a digital accelerometer. For example, because the signals the digital accelerometer would produce signals already in digital format, the digital accelerometer could bypass converter 1364 and electrically couple to the low power microcontroller 1370—in which case multiplexer 1360 would no longer be required. Also, the digital signal may be configured to turn itself on when detecting motion, further conserving power. In addition, continuous step counting may be implemented. The digital accelerometer may include a FIFO buffer to help control the flow of data sent to the low power processor 1370. For instance, data may be buffered in the FIFO until full, at which time the processor may be triggered to turn awaken from an idle state and receive the data.

Low power processor 1370 may be, for example, an MSP430 microcontroller from Texas Instruments. Low power processor 1370 of receiver 800 maintains the idle state, which as stated earlier, requires minimal current draw—e.g., 10 µA or less, or 1 µA or less.

High power processor 1380 may be, for example, a VC5509 digital signal process from Texas Instruments. The high power processor 1380 performs the signal processing actions during the active state. These actions, as stated earlier, require larger amounts of current than the idle state—e.g., currents of 30 µA or more, such as 50 µA or more—and may include, for example, actions such as scanning for conductively transmitted signals, processing conductively transmitted signals when received, obtaining and/or processing physiological data, etc.

The receiver may include a hardware accelerator module to process data signals. The hardware accelerator module may be implemented instead of, for example, a DSP. Being a more specialized computation unit, it performs aspects of the signal processing algorithm with fewer transistors (less cost and power) compared to the more general purpose DSP. The blocks of hardware may be used to "accelerate" the performance of important specific function(s). Some architectures for hardware accelerators may be "programmable" via microcode or VLIW assembly. In the course of use, their functions may be accessed by calls to function libraries.

The hardware accelerator (HWA) module comprises an HWA input block to receive an input signal that is to be processed and instructions for processing the input signal; and, an HWA processing block to process the input signal according to the received instructions and to generate a resulting output signal. The resulting output signal may be transmitted as needed by an HWA output block.

Figure 14:
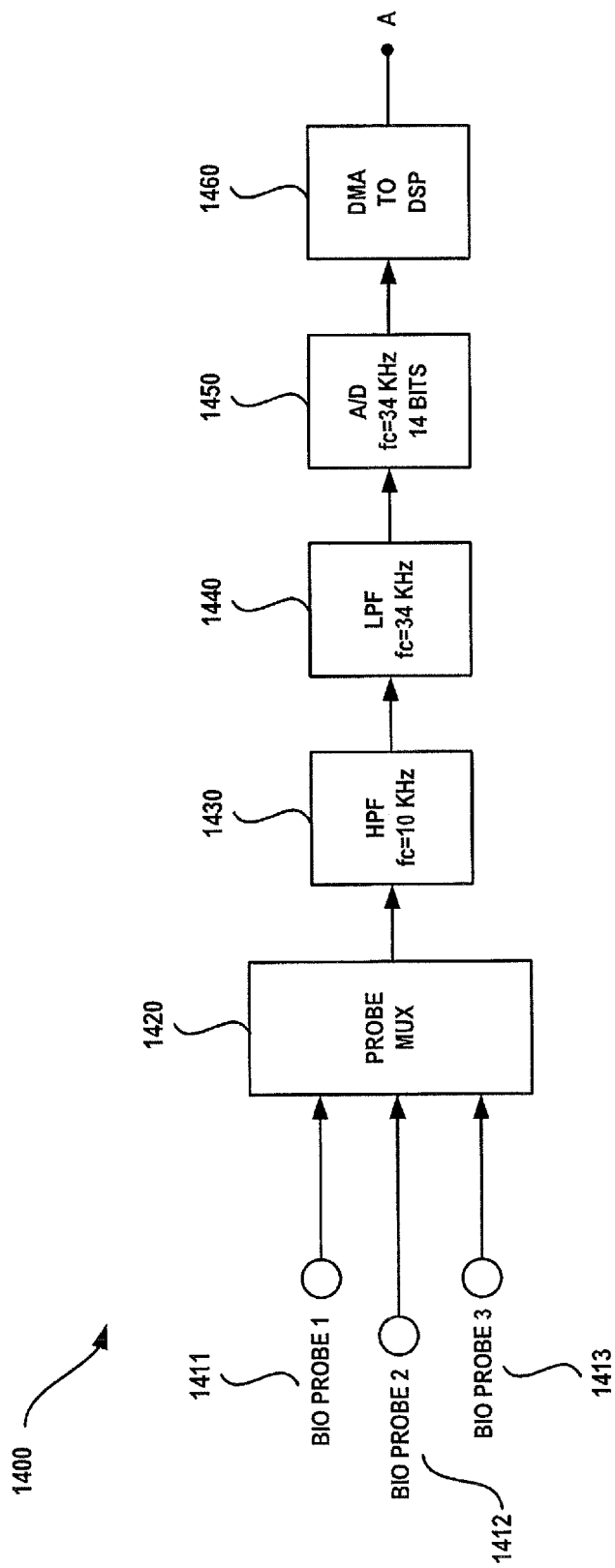
FIG. 14 provides a block diagram of a high frequency signal chain in a receiver, according to one aspect.

FIG. 14 provides a view of a block diagram of hardware in a receiver according to an aspect of the invention related to the high frequency signal chain. In FIG. 14, receiver 1400 includes receiver probes (for example in the form of electrodes 1411, 1412 and 1413) electrically coupled to multiplexer 1420. Also shown are high pass filter 1430 and low pass filter 1440 to provide for a band pass filter which eliminates any out-of-band frequencies. In the aspect shown, a band pass of 10 KHz to 34 KHz is provided to pass carrier signals falling within the frequency band. Example carrier frequencies may include, but are not limited to, 12.5 KHz and 20 KHz. One or more carriers may be present. In addition, receiver 1400 includes analog to digital converter 1450—for example, sampling at 500 KHz. The digital signal can thereafter be processed by the DSP. Shown in this aspect is DMA to DSP unit 1460 which sends the digital signal to dedicated memory for the DSP. The direct memory access provides the benefit of allowing the rest of the DSP to remain in a low power mode.

Figure 15:
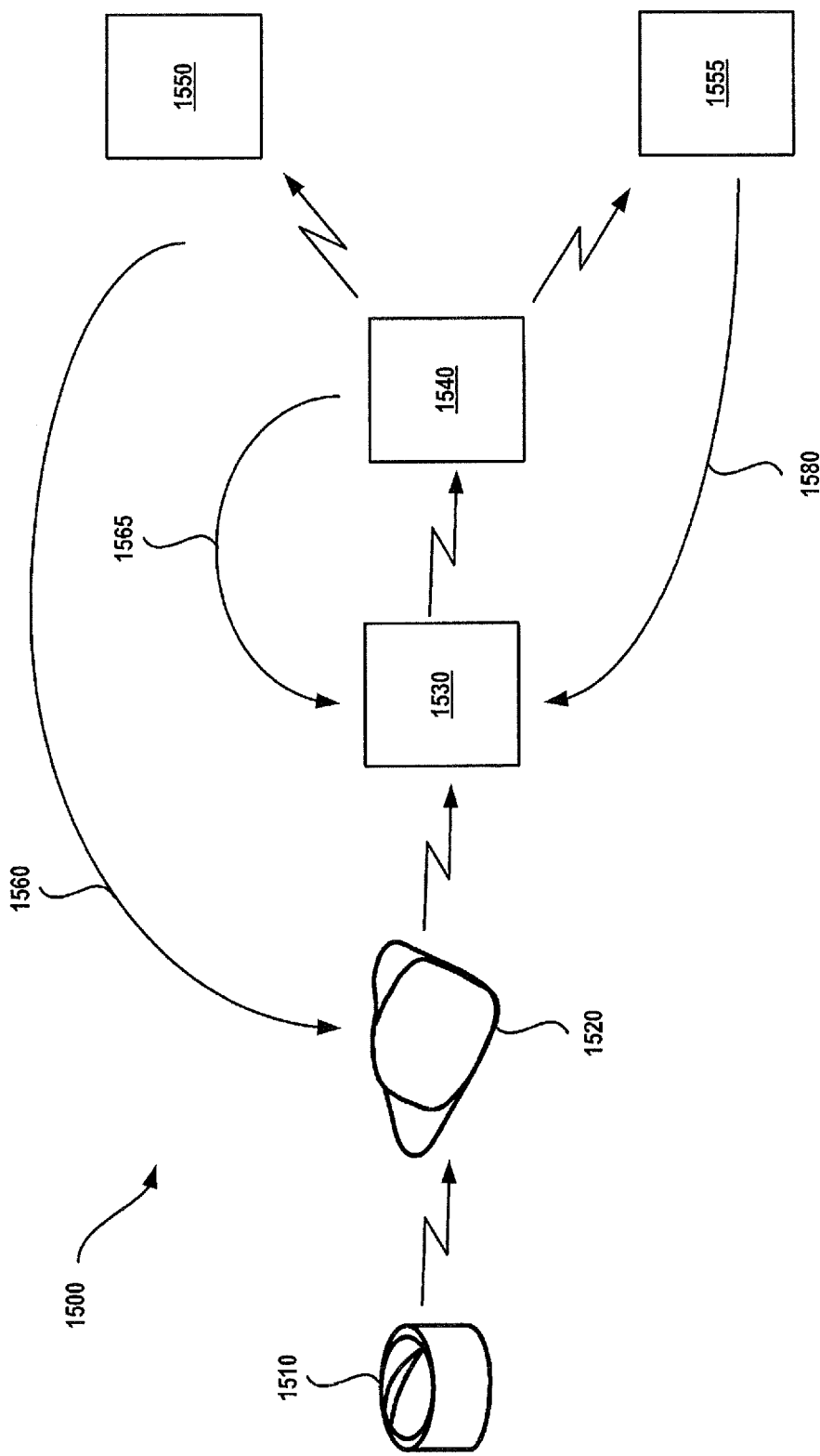
FIG. 15 provides a diagram of how a system that includes a signal receiver and an ingestible event marker may be employed, according to one aspect.

An example of a system of the invention is shown in FIG. 15. In FIG. 15, system 1500 includes a pharmaceutical composition 1510 that comprises an IEM. Also present in system 1500 is signal receiver 1520, such as the signal receiver illustrated in FIGS. 10 to 12. Signal receiver 1520 is configured to detect a signal emitted from the identifier of the IEM 1510. Signal receiver 1520 also includes physiologic sensing capability, such as ECG and movement sensing capability. Signal receiver 1520 is configured to transmit data to a patient's an external device or PDA 1530 (such as a smart phone or other wireless communication enabled device), which in turn transmits the data to a server 1540. Server 1540 may be configured as desired, e.g., to provide for patient directed permissions. For example, server 1540 may be configured to allow a family caregiver 1550 to participate in the patient's therapeutic regimen, e.g., via an interface (such as a web interface) that allows the family caregiver 1550 to monitor alerts and trends generated by the server 1540, and provide support back to the patient, as indicated by arrow 1560. The server 1540 may also be configured to provide responses directly to the patient, e.g., in the form of patient alerts, patient incentives, etc., as indicated by arrow 1565 which are relayed to the patient via PDA 1530. Server 1540 may also interact with a health care professional (e.g., RN, physician) 1555, which can use data processing algorithms to obtain measures of patient health and compliance, e.g., wellness index summaries, alerts, cross-patient benchmarks, etc., and provide informed clinical communication and support back to the patient, as indicated by arrow 1580.

Systems of the invention may include an external device which is distinct from the receiver (which may be implanted or topically applied in certain aspects), where this external device provides a number of functionalities. Such an apparatus can include the capacity to provide feedback and appropriate clinical regulation to the patient. Such a device can take any of a number of forms. By example, the device can be configured to sit on the bed next to the patient, e.g., a bedside monitor. Other formats include, but are not limited to, PDAs, phones, such as smart phones, computers, etc. The device can read out the information described in more detail in other sections of the subject patent application, both from pharmaceutical ingestion reporting and from physiological sensing devices, such as is produced internally by a pacemaker device or a dedicated implant for detection of the pill. The purpose of the external apparatus is to get the data out of the patient and into an external device. One feature of the external apparatus is its ability to provide pharmacologic and physiologic information in a form that can be transmitted through a transmission medium, such as a telephone line, to a remote location such as a clinician or to a central monitoring agency.

Manufacturing Methods

Also provided are methods of manufacturing highly-swellable polymeric films, as well as compositions that include the same. Highly-swellable polymeric films may be prepared as free-standing films in some instances. For example, solvent casting fabrication methods may be employed in which a liquid composition of the one or more polymers, e.g., an alginate, a polyacrylic acid, a blend of the two, etc., may be prepared by combining the polymeric components and a suitable solvent(s). Solvents of interest include, but are not limited to: water and aqueous solvents which include one or more solutes (e.g., salts); organic solvents, e.g., alcohols, such as ethanol, propanol, isopropanol, methanol, butanol, etc.; polyols, e.g., propylene glycol, glycerin, butylene glycol, ethoxydiglycol, polyethylene glycol, methyl or ethyl ethers of diglycols, cyclic polyols, ethoxylated or propoxylated glycols; and other organic solvents, e.g., Heptane, Isobutyl acetate, Butyl acetate, Methylethylketone, tert-Butylmethyl ether, Methylisobutylketone, Dimethyl sulfoxide, Pentane, Toluene, Trichloroethylene, and Xylene; etc. In the liquid composition, the amount of polymer component may vary, ranging in some instances from 1 to 20 weight percent, such as 2 to 10 and including 3 to 4. Additives may be included in the liquid as desired, e.g., binders, plasticizers, porogens, etc., such as described above. The amount of additives that is included, if employed, may vary, and in some instances ranges from 1 to 50%, such as 5 to 10%. The liquid composition may be prepared at any convenient temperature, e.g., 15 to 45° C., using any convenient protocol, e.g., stirring, etc. Following preparation of the liquid composition, the liquid composition may be shaped as desired, e.g., by placing into a mold, by casting on a suitable substrate, etc., following which the solvent is separated from the remainder of the liquid composition to produce the desired film. Solvent separation may be achieved a number of different ways, e.g., via evaporation, which may occur at room temperature or elevated temperatures, such that the temperature may range in some instances from 25 to 100° C., such as 45 to 75° C.

Where desired, following preparation the film may be further treated to provide for desired characteristics, e.g., swellability, solubility, mechanical strength, etc. For example, the film may be contacted with a suitable acidic solution, e.g., HCl, for a period of time sufficient to exchange protons for sodium ions. This can reduce the solubility and swelling nature of the film desired. Contact of the film with the acid may be achieved using any convenient protocol, e.g., dipping the film in the acid solution, spraying the film with the acid solution, etc.

Mechanical strength of the resultant film may be increased in a number of different ways. In some instances, the film may be contacted with a cross-linking agent to enhance the mechanical properties of the film. For example, where the film is an alginate, such as sodium alginate, the film may be contacted (such as by spraying) with a divalent cation solution, such as $CaCl_2$, $MgCl_2$, etc. Alternatively, the alginate may be contacted with a basic solution, e.g., sodium hydroxide, to enhance the mechanical properties of the film.

For ingestible compositions that include a highly-swellable polymeric film and a second component, e.g., as described herein, aspects of the methods include combining an ingestible component (which may or may not include a device, such as an IEM) and a highly-swellable polymeric film, e.g., as described above, in a manner sufficient to produce a desired ingestible composition. Any convenient manufacturing protocol may be employed, where protocols of interest include both manual and automated protocols, as well as protocols that include both manual and automated steps. Protocols of interest that find use in various aspects of the fabrication methods described herein include lamination, molding, pressing, extrusion, stamping, coating (such as spray coating and dipping), gluing, etc. In some instances, fabrication protocols as described in PCT application serial nos. PCT/US2010/020142 published as WO 2010/080765; PCT/US2006/016370 published as WO 2006/116718 and PCT/US2008/077753 published as WO2009/042812 (the disclosures of which applications are herein incorporated by reference); are employed.

Aspects of the fabrication protocols include stably associating the ingestible component with a highly-swellable polymeric film component. By "stably associating" is meant that the ingestible component and highly-swellable polymeric film component do not separate from each other, at least until desired during intended use, e.g., upon administration to a subject in need thereof, such as by ingestion. Any convenient approach for stably associating the ingestible component and the highly-swellable polymeric film component may be employed.

Where an ingestible event marker having one of its dissimilar materials covered by a highly-swellable polymeric film is desired, e.g., as illustrated in FIGS. 7 to 9B, a protocol in which a pre-fabricated film, e.g., prepared as described above, may be employed. In such a protocol, a dissimilar material of the ingestible event marker may be contacted with a pre-fabricated highly-swellable polymeric film in a manner sufficient to cover the dissimilar material with the film. Where desired, an adhesive may be employed to secure the components together.

In a variation of the above protocol, a fabrication process may be one in which the highly-swellable polymeric film is fabricated at the same time that the ingestible component is stably associated therewith. For example, a molding process may be employed where liquid film precursor composition, e.g., as described above, is positioned in a mold, followed by placement of an ingestible component (e.g., IEM) on the precursor material. The solvent component of the liquid composition may be removed to associate the film with the dissimilar material of the ingestible event marker. Temperature modulation may be employed where appropriate. Following solidification of the precursor material, the resultant final product may be removed from the mold.

In yet another fabrication protocol of interest, a stamping protocol may be employed. For example, an ingestible component may be positioned between two sheets of prefabricated highly-swellable polymeric films. Once positioned between the two sheets, a stamping tool may be used to stamp and seal the two sheets around the ingestible component in a manner that encases the ingestible component in a sealed multilayer of the highly-swellable polymeric film. The stamping tool may be configured to produce a product having any convenient shape, such as a disc, etc. Where desired, temperature modulation may be employed in such protocols.

In yet another fabrication protocol of interest, a coating process may be employed to stably associate the ingestible component with the highly-swellable polymeric film component. For example, a premade ingestible component in the form of a tablet may be provided, e.g., as described in PCT application serial nos. PCT/US2010/020142 published as WO 2010/080765; PCT/US2006/016370 published as WO 2006/116718 and PCT/US2008/077753 published as WO2009/042812; the disclosures of which applications are herein incorporated by reference. This premade ingestible component may then be spray coated with a liquid precursor composition (e.g., as described above). Following spray coating, the coating material may be allowed to harden (e.g., by maintaining the coated tablet at a suitable temperature, such as room temperature) to produce the desired product.

Where desired, aspects of the above described or other suitable protocols may be combined to produce a fabrication protocol. For example, a molding process may be employed to make a product and the product spray coated with a further material, such as a soluble material.

Methods of Use

Aspects of the invention further include methods of using the compositions, such as those described above. Aspects of such methods include administering an ingestible composition to a subject, e.g., by self-administration or via the assistance of another, such as a health care practitioner. Such methods may include placing the ingestible composition in the mouth of a subject such that the subject swallows the ingestible composition. In this manner, the subject ingests the ingestible composition. Ingestible compositions may be employed with a variety of subjects. Subjects of interest include "mammals" including animals classified in the orders carnivore (e.g., dogs and cats), rodentia (e.g., mice, guinea pigs, and rats), and primates (e.g., humans, chimpanzees, and monkeys). In certain aspects, the subjects will be humans.

Following ingestion, the methods may include receiving a signal emitted from an ingestible composition, such as an IEM comprising ingestible composition, e.g., at a receiver, such as described above. In some instances, the received signal is a conductively transmitted signal.

Ingestible compositions may be employed in a variety of different applications. Applications of interest in which the ingestible composition comprises an IEM include, but are not limited to: monitoring patient compliance with prescribed therapeutic regimens; tailoring therapeutic regimens based on patient compliance; monitoring patient compliance in clinical trials; monitoring usage of controlled substances; monitoring the occurrence of a personal event of interest, such as the onset of symptoms, etc., and the like. Applications of interest are further described in PCT Application Serial No. PCT/US2006/016370 published as WO/2006/116718; PCT Application Serial No. PCT/US2007/082563 published as WO/2008/052136; PCT Application Serial No. PCT/US2007/024225 published as WO/2008/063626; PCT Application Serial No. PCT/US2007/022257 published as WO/2008/066617; PCT Application Serial No. PCT/US2008/052845 published as WO/2008/095183; PCT Application Serial No. PCT/US2008/053999 published as WO/2008/101107; PCT Application Serial No. PCT/US2008/056296 published as WO/2008/112577; PCT Application Serial No. PCT/US2008/056299 published as WO/2008/112578; and PCT Application Serial No. PCT/US2008/077753 published as WO2009/042812; the disclosures of which applications is herein incorporated by reference.

Kits

Also provided are kits that include one or more ingestible compositions, such as described above. In those aspects having a plurality of ingestible compositions, the ingestible compositions may be packaged in a single container, e.g., a single tube, bottle, vial, and the like, or one or more dosage amounts may be individually packaged such that certain kits may have more than one container of ingestible compositions. In certain aspects the kits may also include a receiver, such as reviewed above. In certain aspects, the kits may also include an external monitor device, e.g., as described above, which may provide for communication with a remote location, e.g., a doctor's office, a central facility etc., which obtains and processes data obtained about the usage of the composition.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other aspects, the instructions are present as an electronic storage data file present on a suitable computer readable storage medium, e.g. CD-ROM, diskette, etc. In yet other aspects, the actual instructions are not present in the kit, but means for obtaining the instructions from a remote source, e.g. via the internet, are provided. An example of this aspect is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many aspects of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

The following examples are offered by way of illustration and not by way of limitation.

Experimental

As an example, a free standing film consisting of a mixture of sodium alginate and cross-linked poly acrylic acid can be formed by creating an aqueous solution of the two components and casting into a recessed mold. For example, 1.5 g of sodium alginate and 0.5 g of cross-linked polyacrylic acid may be added to a beaker of water under constant stirring. Once both components are fully dissolved, this viscous solution is poured into a Teflon® coated mold to a desired thickness, and placed into an oven to dry at 45° C. Once dried, the remaining polymer solids can be removed from the mold as a free standing film.

The free standing alginate/polyacrylic acid film can then be heat press laminated to existing IEM sensor sheets of the same lateral form factor. A wide range of equipment can be utilized to create this laminate, and specific conditions ultimately depend on the film composition, but generally pressing temperatures from 130-150° C. and moderate pressures (e.g., 50 to 100 psi) are sufficient to thermally bond the film to the IEM sensor sheet. The film and IEM sensor sheet are placed into the press or roll laminator with non-stick liners made of a fluorinated polymer (Teflon or fluorinated ethylene propylene (FEP)) placed on both the top and bottom of the film stack. Following pressing, the assembled stack is cooled and individual IEM sensors with alginate/polyacrylic acid overlayers can be singulated to a variety of form factors by mechanically punching the film stack.

Currently, these films are showing a robust ability to provide moisture protection at humidities considered very aggressive to the battery material on the IEM sensor. For example, the cuprous chloride battery material for a standard IEM will have completely degraded is battery charge due to moisture related reaction in ~10 days at 25° C. and 70% relative humidity. IEMs with an alignate/polyacrylic acid film show minimal degradation of cupric chloride battery material at 25° C. and 70% relative humidity for over 28 days of aging.

It is to be understood that this invention is not limited to particular aspects described, as such may vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which may be readily separated from or combined with the features of any of the other several aspects without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

What is claimed is:

1. A device comprising: a highly-swellable polymeric film that rapidly swells without disintegrating upon contact with an aqueous medium external to the device; an ingestible component comprising a partial power source comprising an anode material and a cathode material, the anode material comprising at least one of magnesium, zinc, sodium, lithium, iron, or alloys thereof, or cuprous iodine or cuprous chloride; and the cathode material comprising at least one of copper salts of iodide, chloride, bromide, sulfate, formate, or $Fe^{3+}$ salts, or silver salts, or magnesium metal or magnesium alloy; and a protective barrier positioned on top of the highly-swellable polymeric film, wherein the protective barrier is further positioned to at least partially expose a side of the highly-swellable polymeric film, wherein the highly-swellable polymeric film is pre-fabricated to:

in a first mode of operation, cover the anode material to inhibit reaction of the anode material with ambient moisture; and in a second mode of operation, upon contact with the aqueous medium via the at least partially exposed side, the highly-swellable polymeric film rapidly swells to disrupt the protective barrier, thereby forming a conductive film over the anode material and the cathode material to provide conduction between the aqueous medium and the anode material and the cathode material.

2. The device according to claim 1, wherein the film rapidly swells to ten times or greater in volume upon contact with the aqueous medium.

3. The device according to claim 2, wherein the film swells to ten times or greater in volume within one minute or less upon contact with the aqueous medium.

4. The device according to claim 1, wherein the film is configured to absorb ten grams or more of water per gram of film upon contact the aqueous medium.

5. The device according to claim 1, wherein the film comprises an ionic polymer.

6. The device according to claim 5, wherein the ionic polymer is a polysaccharide.

7. The device according to claim 6, wherein the polysaccharide is an alginate.

8. The device according to claim 7, wherein the film further comprises a carboxyl functional group.

9. The device according to claim 8, wherein the film comprises a polyacrylic acid.

10. The device according to claim 1, wherein the film comprises cross-linked polymers.

11. The device according to claim 1, wherein the film further comprises a porogen.

12. The device according to claim 1, wherein the film has a thickness of ten microns or greater.

13. The device according to claim 1, wherein the film is stably associated with an ingestible event indicator.

14. The highly-swellable polymeric film according to claim 1, wherein in the second mode of operation, the conductive film impedes contact between a non-conductive entity and the anode material and the cathode material.

15. An ingestible device comprising:
an ingestible component sized to be minimally dimensioned for ingestion, wherein the ingestible component comprises a partial power source comprising an anode material and a cathode material, the anode material comprising at least one of magnesium, zinc, sodium, lithium, iron, or alloys thereof, or cuprous iodine or cuprous chloride; and the cathode material comprising at least one of copper salts of iodide, chloride, bromide, sulfate, formate, or Fe3+ salts, or silver salts, or magnesium metal or magnesium alloy;
a highly-swellable polymeric film stably associated with the ingestible component; and
a protective barrier positioned on top of the highly-swellable polymeric film, wherein the protective barrier is further positioned to at least partially expose a side of the highly-swellable polymeric film,
wherein the highly-swellable polymeric film is pre-fabricated to:
in a first mode of operation, cover the anode material to inhibit reaction of the anode material with ambient moisture; and
in a second mode of operation, upon contact with an external aqueous medium via the at least partially exposed side, the highly-swellable polymeric film rapidly swells without disintegrating to disrupt the protective barrier, thereby forming a conductive film over the anode material and the cathode material to provide conduction between the aqueous medium and the anode material and the cathode material.

16. The ingestible device according to claim 15, wherein the highly swellable polymeric film rapidly swells to ten times or greater in volume upon contact with the aqueous medium.

17. The ingestible device according to claim 15, wherein the ingestible component comprises circuitry.

18. The ingestible device according to claim 15, wherein the ingestible component is an ingestible event indicator.

19. The ingestible device according to claim 18, wherein the ingestible event indicator comprises:
a support; and
circuitry associated with the support wherein:
the anode material is electrically coupled to the circuitry and associated with the support;
the cathode material is electrically coupled to the circuitry, is associated with the support, and is electrically isolated from the first anode material; and
the anode material and cathode material are selected to provide a voltage potential difference when in contact with a conducting fluid.

20. The ingestible device according to claim 19, wherein the highly-swellable polymeric film is associated with the support and is configured as a signal amplification that increases a length of a current path between the anode material and cathode material.

21. The ingestible device according to claim 20, wherein the ingestible device further comprises an active agent.

22. The ingestible device according to claim 21, wherein the ingestible device further comprises a pharmaceutically acceptable carrier.

23. The ingestible device according to claim 22, wherein the highly-swellable polymeric film is configured to separate the event indicator from the pharmaceutically acceptable carrier upon swelling.

24. A system comprising:
an ingestible device comprising:
an ingestible component sized to be minimally dimensioned for ingestion, wherein the ingestible component comprises a partial power source comprising an anode material and a cathode material, the anode material comprising at least one of magnesium, zinc, sodium, lithium, iron, or alloys thereof, or cuprous iodine or cuprous chloride; and the cathode material comprising at least one of copper salts of iodide, chloride, bromide, sulfate, formate, or Fe3+ salts, or silver salts, or magnesium metal or magnesium alloy; and
a highly-swellable polymeric film stably associated with the ingestible component, and;
a protective barrier positioned on top of the highly-swellable polymeric film, wherein the protective barrier is further positioned to at least partially expose a side of the highly-swellable polymeric film,
wherein upon contact with an external aqueous medium via the at least partially exposed side, the highly-swellable polymeric film is pre-fabricated to:
in a first mode of operation, cover the anode material to inhibit reaction of the anode material with ambient moisture; and in a second mode of operation, the highly-swellable polymeric film rapidly swells without disintegrating to disrupt the protective barrier, thereby forming a conductive film over the anode material and the cathode material to provide conduction between the aqueous medium and the anode material and the cathode material; and a receiver configured to receive a communication associated with the ingestible component.

25. A method comprising:

accessing an ingestible component comprising a protective barrier, wherein the ingestible component comprises a partial power source comprising an anode material and a cathode material, the anode material comprising at least one of magnesium, zinc, sodium, lithium, iron, or alloys thereof, or cuprous iodine or cuprous chloride; and the cathode material comprising at least one of copper salts of iodide, chloride, bromide, sulfate, formate, or Fe3+ salts, or silver salts, or magnesium metal or magnesium alloy;

accessing a highly-swellable polymeric film;

combining the ingestible component and the highly-swellable polymeric film, such that the protective barrier is positioned on top of the highly-swellable polymeric film, such that the protective barrier at least partially exposes a side of the highly-swellable polymeric film, wherein the highly-swellable polymeric film is pre-fabricated to:

in a first mode of operation, cover the anode material to inhibit reaction of the anode material with ambient moisture, and in a second mode of operation, upon contact with an external aqueous medium via the at least partially exposed side, the highly-swellable polymeric film rapidly swells without disintegrating to disrupt the protective barrier, thereby forming a conductive film over the anode material and the cathode material to provide conduction between the aqueous medium and the anode material and the cathode material.

26. The method according to claim 25, wherein the ingestible component is an ingestible event indicator.

27. The method according to claim 25, wherein the method comprises stably associating the ingestible component and the film.

28. The method according to claim 25, wherein the method comprises one or more protocols selected from the group consisting of laminating, pressing, stamping, extruding, molding, gluing and coating.

29. The method according to claim 25, wherein at least a portion of the method is automated.

* * * * *